Figure 6:
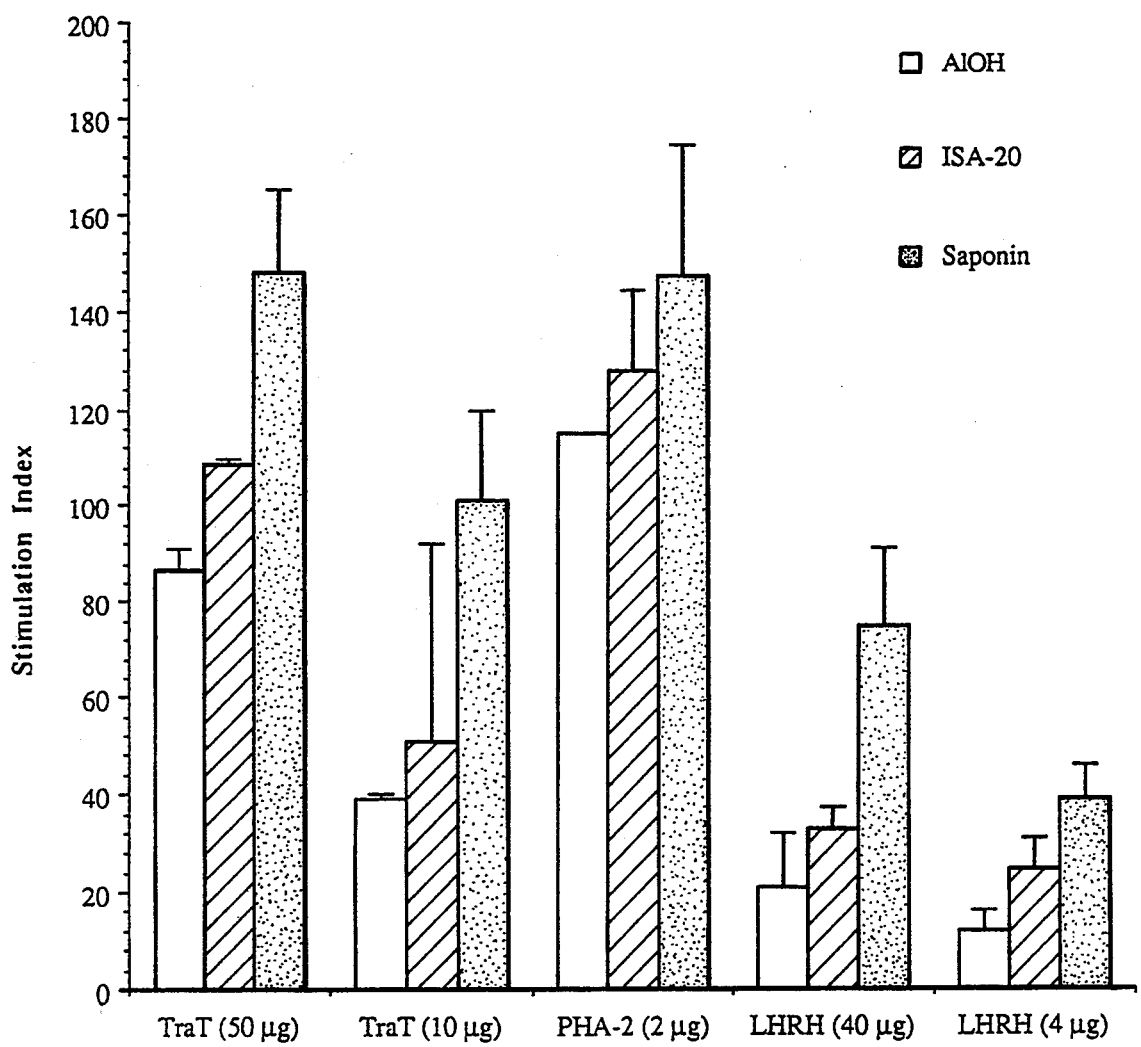

United States Patent [19]

Russell-Jones et al.

[11] Patent Number: 5,403,586
[45] Date of Patent: Apr. 4, 1995

[54] LHRH-TRATP FUSION PROTEINS

[75] Inventors: Gregory J. Russell-Jones, Middle Cove; Andrew G. Stewart, Pymble; Con G. Tsonis, Denistone, all of Australia

[73] Assignee: Biotechnology Australia Ptl Ltd., Roseville, Australia

[21] Appl. No.: 690,983
[22] PCT Filed: Aug. 24, 1990
[86] PCT No.: PCT/AU90/00373
  § 371 Date: Jun. 25, 1991
  § 102(e) Date: Jun. 25, 1991
[87] PCT Pub. No.: WO91/02799
  PCT Pub. Date: Mar. 7, 1991

[30] Foreign Application Priority Data

Aug. 25, 1989 [AU] Australia .................. PJ5979

[51] Int. Cl.$^6$ ........................... A61K 39/00
[52] U.S. Cl. ................... 424/192.1; 424/198.1; 424/811; 435/69.3; 435/69.4; 435/69.7; 435/252.3; 435/320.1; 536/23.4; 930/130
[58] Field of Search ............. 435/253, 69.4, 172.3, 435/320.1, 69.3; 935/72, 73; 514/2, 15, 12; 530/313, 350; 424/192.1, 198.1, 811; 536/23.4

[56] References Cited

U.S. PATENT DOCUMENTS 4,624,926 11/1986 Inouye et al. .................. 435/253

FOREIGN PATENT DOCUMENTS

| 0293530 | 7/1988 | European Pat. Off. | C07K 7/20 |
| 8706590 | 4/1987 | WIPO | C07K 15/04 |
| 8800056 | 1/1988 | WIPO | A61K 37/43 |
| 8805308 | 7/1988 | WIPO | A61K 39/385 |

Primary Examiner—Garnette D. Draper
Assistant Examiner—L. Spector
Attorney, Agent, or Firm—Foley & Lardner

[57] ABSTRACT

This invention relates to the preparation of novel fusion proteins which comprise an analogue of LHRH and TraTp or an analogue of TraTp. The fusion proteins of the invention are useful as components of vaccines for the inhibition or control of reproductive functions in vertebrate hosts. The invention also relates to polynucleotide molecules encoding the fusion proteins, to transformant hosts expressing the fusion proteins and to methods of inhibiting or controlling reproductive function in vertebrate hosts using the fusion proteins or vaccines of the invention.

17 Claims, 15 Drawing Sheets

FIG. 1B

AGATCTCTCACCTACCAAAACAATGCCCCCTGCAAAAAATAAATTCATATAAAAA

Operator-13                    Operator-12
ACATACAGATAACCATCTGCGGTGATAAATTATCTCTGGCGGTGTTGACATAAATACCAC Operator-11            mRNA----->                    TraT, 5' untranslated----->
TGGCGGTGATACTGAGCAC ATCAGCAGG/AATTCTATGGTTATAGTTCAAAACGATAT
                               EcoRI GATGAGTGAATCTTAATTTGTATATTATGACGTTTATTCAATATGAAGGAACATTG ATG
                                                          TraT

FIG. 2A

TO FIG. 2B →

```
1                                                31
ATG AAA ATG AAA AAA TTG ATG ATG GTT GCA CTG GTC AGT TCC ACT
Met Lys Met Lys Lys Leu Met Met Val Ala Leu Val Ser Ser Thr
                                                  signal sequence 91                                               121
CGT AAC CTT GAG GTG AAG ACT CAG ATG AGT GAG ACC ATC TGG CTT
Arg^Asn Leu Glu Val Lys Thr Gln Met Ser Glu Thr Ile Trp Leu
new PvuII 181                                              211
TCT GAT AAA GAC ATG AGT GGG CTG CAG GGC AAA ATT GCT GAT GCT
Ser Asp Lys Asp Met Ser Gly Leu Gln Gly Lys Ile Ala Asp Ala 271                                              301
TAC TAC TGG ATT CAG GCG AAT GTG CTG AAG GCC GAT AAG ATG GAT
Tyr Tyr Trp Ile Gln Ala Asn Val Leu Lys Ala Asp Lys Met Asp
                                            HaeII 361                                              391
GCA GTT GGT GCA GCG TTA GGT GCC GGT ATT ACC GGT TAT AAC TCA
Ala Val Gly Ala Ala Leu Gly Ala Gly Ile Thr Gly Tyr Asn Ser 451                                              481
GTG GGT ATG GCT GCA GAT GCG ATG GTG GAA GAT GTG AAC TAT ACC
Val Gly Met Ala Ala Asp Ala Met Val Glu Asp Val Asn Tyr Thr 541                                              571
ACA ACG GAT AAT GTT GCC GCC CTG CGT CAG GGC ACA TCA GGT GCG
Thr Thr Asp Asn Val Ala Ala Leu Arg Gln Gly Thr Ser Gly Ala 631                                              661
ACC CGT GTG GTT TCA AAT GCG AAC AAG GTT AAC CTG AAA TTT
Thr Arg Val Val Ser Asn Ala Asn Lys Val Asn Leu Lys Phe
                                       HpaI 721
AAT ATT CTC TGA
Asn Ile Leu ***
SepI   243
```

```
                     61
        CTG GCC CTT TCA GGG TGT GGT GCG ATG AGC ACA GCA ATC AAG AAG
        Leu Ala Leu Ser Gly Cys Gly Ala Met Ser Thr Ala Ile Lys Lys
                                                                  30
                    151
        GAA CCC GCC AGC GAA CGC ACG GTA TTT CTG CAG ATC AAA AAC ACG
        Glu Pro Ala Ser Glu Arg Thr Val Phe Leu Gln Ile Lys Asn Thr
                                                                  60
                    241
        GTG AAA GCA AAA GGA TAT CAG GTG GTG ACT TCT CCG GAT AAA GCC
        Val Lys Ala Lys Gly Tyr Gln Val Val Thr Ser Pro Asp Lys Ala
                         EcoRV                                    90
                    331
        CTG CGG GAG TCT CAG GGA TGG CTG AAC CGT GGT TAT GAA GGC GCA
        Leu Arg Glu Ser Gln Gly Trp Leu Asn Arg Gly Tyr Glu Gly Ala
                                                                 120
                    421
     AAT TCT GCC GGT GCC ACA CTC GGT GTA GGC CTT GCT GCT GGT CTG
     Asn Ser Ala Gly Ala Thr Leu Gly Val Gly Leu Ala Ala Gly Leu
                                             Stu I              150
                    511
     ATG ATC ACG GAT GTA CAG ATT GCA GAG CGT ACT AAG GCA ACG GTG
     Met Ile Thr Asp Val Gln Ile Ala Glu Arg Thr Lys Ala Thr Val
                                              BsaI              180
                    601
     AAA ATT CAG ACC AGT ACT GAA ACA GGT AAC CAG CAT AAA TAC CAG
     Lys Ile Gln Thr Ser Thr Glu Thr Gly Asn Gln His Lys Tyr Gln
                         ScaI                                   210
                    691
    GAA GAG GCG AAG CCT GTT CTC GAA GAC CAA CTG GCC AAA TCA ATC GCA
    Glu Glu Ala Lys Pro Val Leu Glu Asp Gln Leu Ala Lys Ser Ile Ala
                                                  BalI
                                                                 240
```

TO FIG. 2A

FIG. 3A

TraTp-LHRH FUSION PROTEINS pBTA 609

```
TraT ──→        LHRH ──────────────────────────────────→   TraT ──→
AAG.AAG.CAG. GAG.CAC.TGG.TCA.TAT.GGT.CTG.CGT.CCC.GGG.CTG.CTT.GAG.
Lys Lys  Gln  Glu  His Trp Ser Tyr Gly Leu Arg Pro Gly Leu Leu Glu
    30                                                     33
``` pBTA 732

```
TraT ──→             LHRH ──────────────────────────────→          TraT
AAA.GGA.TCC.CCC.GAG.CAC.TGG.TCA.TAT.GGT.CTG.CGT.CCC.GGG.GAG.CAT.CAG.
Lys Gly Ser Pro Glu His Trp Ser Tyr Gly Leu Arg Pro Gly Glu His Gln
    80                                                          82
``` pBTA 735

```
TraT──→         LHRH ──────────────────────────────→               TraT
AAG.GCC.CCC.GAG.CAC.TGG.TCA.TAT.GGT.CTG.CGT.CCC.GGG.GGG.AGC.TCC.GAT
Lys Ala Pro Glu His Trp Ser Tyr Gly Leu Arg Pro Gly Gly Ser Ser Asp
    101                                                         102
``` pBTA 737

```
TraT──→             LHRH ──────────────────────────────→           TraT──→
GTA.GGA.GCT.CCC.GAG.CAC.TGG.TCA.TAT.GGT.CTG.CGT.CCC.GGG.GGG.GGC.CTT.GCT
Val Gly Ala Pro Glu His Trp Ser Tyr Gly Leu Arg Pro Gly Gly Gly Leu Ala
    145                                                         146
```

FIG. 3B

```
pBTA 734
TraT ─────→┌── LHRH ──┐┌─────── TraT ───────
GAG.CGT.GAG.CAC.TGG.TCA.TAT.GGT.CTG.CGT.CCC.GGG.ACT.AAG.
Glu Arg Glu His Trp Ser Tyr Gly Leu Arg Pro Gly Thr Lys
175                                                  176 pBTA 733
TraT ─────→┌── LHRH ──┐┌─────── TraT ───────
ACC.AGT.GAG.CAC.TGG.TCA.TAT.GGT.CTG.CGT.CCC.GGG.ACT.GAA.
Thr Ser Glu His Trp Ser Tyr Gly Leu Arg Pro Gly Thr Glu
200                                                  201 pBTA 731
TraT ─────→┌── LHRH ──┐┌─────── TraT ───────
AAG.GTT.GAG.CAC.TGG.TCA.TAT.GGT.CTG.CGT.CCC.GGG.AAC.CTG
Lys Val Glu His Trp Ser Tyr Gly Leu Arg Pro Gly Asn Leu
220                                                  221 pBTA 740
TraT ─────→┌──────── LHRH ────────┐┌─────────────── TraT ───────────────
CAA.CTG.GCC.CCC.GAG.CAC.TGG.TCA.TAT.GGT.CTG.CGT.CCC.GGG.GGG.AGC.TCC.AAA
Gln Leu Ala Pro Glu His Trp Ser Tyr Gly Leu Arg Pro Gly Gly Ser Ser Lys
236                                                                  237 pBTA 730
TraT ─────→┌──────── LHRH ────────┐┌─────── TraT ───────
GCA.AAT.GAG.CAC.TGG.TCA.TAT.GGT.CTG.CGT.CCC.GGG.ATT.CTC.TGA
Ala Asn Glu His Trp Ser Tyr Gly Leu Arg Pro Gly Ile Leu ***
241                                                  242
```

FIG. 4A

Sequence of DNA fragments coding for LHRH.

```
                                              Smal
GAG  CAC  TGG  TCA  TAT  GGT  CTG  CGT  CCC  GGG
GTC  GTG  ACC  AGT  ATA  CCA  GAC  GCA  GGG  CCC
Glu  His  Trp  Ser  Tyr  Gly  Leu  Arg  Pro  Gly
```

FIG. 4B

Sequence of linker DNA.

```
         Smal
    CCCCCGGGAGCT
    GGGGGCCCTCGA
```

FIG. 4C

Sequence of LHRH DNA used in the construction of pBTA 870.

```
GGT  GAA  CAT  TGG  AGC  TAC  GGT  CTA  CGC  CCC
CCA  CTT  GTA  ACC  TCG  ATG  CCA  GAT  GCG  GGG
Gly  Glu  His  Trp  Ser  Tyr  Gly  Leu  Arg  Pro
```

FIG. 4D

```
GGT.GAA.CAC.TGG.TCT.TAT.GGC.TTA.CGG.CCG.GGA.GAG.CAT.TGG.AGT.TAC.
CCA.CTT.GTG.ACC.AGA.ATA.CCG.AAT.GCC.GGC.CCT.CTC.GTA.ACC.TCA.ATG.
Gly Glu His Trp Ser Tyr Gly Leu Arg Pro Gly Glu His Trp Ser Tyr

GGC.CTC.CGT.CCC
CCG.GAG.GCA.GGG
Gly Leu Arg Pro
```

FIG. 5A

Sequence of multimers of LHRH in TraT pBTA 870

```
       TraT ——→ ←—————————— LHRH #1 ——————————→
       ACC.AGT.GAG.CAC.TGG.TCA.TAT.GGT.CTG.CGT.CCC.GGT
       Thr Ser Glu His Trp Ser Tyr Gly Leu Arg Pro Gly
           200

←————————— LHRH #2 —————————————→ TraT ——→
    GAA.CAT.TGG.AGC.TAC.GGT.CTA.CGC.CCC.GGG ACT.GAA.
    Glu His Trp Ser Tyr Gly Leu Arg Pro Gly  Thr Glu
                                                201
``` pBTA 862

```
      TraT ——→ ←—————————— LHRH #1 ——————————→
      ACC.AGT.GAG.CAC.TGG.TCA.TAT.GGT.CTG.CTG.CCC.GGT
      Thr Ser Glu His Trp Ser Tyr Gly Leu Arg Pro Gly
          200

←————————————— LHRH #2 ——————————————→
    GAA.CAT.TGG.AGC.TAC.GGT.CTA.CGC.CCC.GGT
    Glu His Trp Ser Tyr Gly Leu Arg Pro Gly

←————————————— LHRH #3 ——————————————→
    GAA.CAC.TGG.TCT.TAT.GGC.TTA.CGG.CCG.GGA.GAG.CAT.TGG.AGT.TAC.GGC.CTC.CGT.CCC.GGG
    Glu His Trp Ser Tyr Gly Leu Arg Pro Gly Glu His Trp Ser Tyr Gly Leu Arg Pro Gly

←———— LHRH #4 ————→ TraT ——→
                        ACT.GAA
                        Thr Glu
                          201
```

FIG. 5B pBTA 859

```
TraT ─────┬─── LHRH#1 ─────────────────────┬──── LHRH#2 ─────────────────────┐
ACC.AGT.GAG.CAC.TGG.TCA.TAT.GGT.CTG.CGT.CCC.GGT.GAA.CAT.TGG.AGC.TAC.GGT.CTA.CGC.CCC.GGT
Thr Ser Glu His Trp Ser Tyr Gly Leu Arg Pro Gly Glu His Trp Ser Tyr Gly Leu Arg Pro Gly
            200

├──── LHRH #3 ────────────────────┬──── LHRH #4 ────────────────────┐
GAA.CAC.TGG.TCT.TAT.GGC.TTA.CGG.CCG.CTC.CGT.CCC.GGT.GAA.GAG.CAT.TGG.AGT.TAC.GGC.CTC.CGT.CCC.GGT
Thr His Trp Ser Tyr Gly Leu Arg Pro Gly Glu His Trp Ser Tyr Gly Leu Arg Pro Gly

├──── LHRH #5 ────────────────────┬──── LHRH #6 ────────────────────┐
GAA.CAC.TGG.TCT.TAT.GGC.TTA.CGG.CCG.GGA.GAG.CAT.TGG.AGT.TAC.GGC.CTC.CGT.CCC.GGT
Glu His Trp Ser Tyr Gly Leu Arg Pro Gly Glu His Trp Ser Tyr Gly Leu Arg Pro Gly

├──── LHRH#7 ────────────────────┬──── LHRH#8 ────────────────────┬── TraT ──┐
GAA.CAC.TGG.TCT.TAT.GGC.TTA.CGG.CCG.GGA.GAG.CAT.TGG.AGT.TAC.GGC.CTC.CGT.CCC.GGG.ACT.GAA
Glu His Trp Ser Tyr Gly Leu Arg Pro Gly Glu His Trp Ser Tyr Gly Leu Arg Pro Gly Thr Glu
                                                                                    201
```

LHRH-TRATP FUSION PROTEINS

This application is filed under 35 U.S.C. §371 claiming priority to PCT application PCT/AU90/00373, filed Aug. 24, 1990 and published Mar. 7, 1991 as WO 91/02799.

TECHNICAL FIELD

This invention relates to fusion proteins useful as components of vaccines for the immunological castration or inhibition of reproductive function of vertebrate hosts in general and domesticated animals in particular.

BACKGROUND ART

The most popular method of preventing reproductive activity in domestic animals, including dogs, horses, sheep, cattle, goats and cats, is surgical ovariohysterectomy or castration.

This method suffers from the problem that it is irreversible and is, technically, a relatively difficult procedure, therefore requiring the skills of trained veterinarians.

One of the alternative methods to surgery is the administration of progestagen steroids which can be used as long term oestrus suppressants (Harris and Wotchuk Am. J. Vet. Res. 24: 1003–1006, 1963) in dogs, but are unfortunately associated with the induction of uterine disorders including pyometritis, endometritis and increased incidence of benign mammary tumours following long term treatment. Their use has therefore tended to become confined to short term suppression of oestrus or postponement of oestrus.

In economically important farm animals there is no commonly used long term contraceptive which has been found to be suitable for routine use in the field.

There is therefore a need for a well-tolerated nonsteroidal method of contraception in domestic animals which is applicable to both male and female domestic animals.

One such method would be to immunise against the hormones which control the development and activity of the reproductive organs.

The two gonadotrophic hormones which regulate gonadal steroidogenesis and gametogenesis, and are responsible for reproductive cyclicity are luteinizing hormone (LH) and follicle stimulating hormone (FSH).

Luteinizing hormone releasing hormone (LHRH, also known as GnRH) controls the synthesis and release of LH and FSH from the anterior pituitary gland. Mammalian LHRH is a decapeptide comprised of naturally occurring amino acids in the following sequence (ID NO: 1):

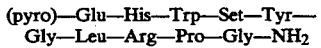
(pyro)—Glu—His—Trp—Ser—Tyr—
Gly—Leu—Arg—Pro—Gly—NH₂

The N and C terminal glutamic acid and glycine residues are modified after translation to pyroglutamic acid and glycinamide respectively. Vaccines which result in the production of antibodies against LHRH by a host will suppress that host's endogenous LH and FSH production and release. This suppression can result in reduction of steroidogenesis and a failure of reproductive cyclicity and fertility in the treated animal. The resultant physiological effects are
(a) in the female:
(i) a cessation of LH pulsatility,
(ii) a failure of ovulation leading to infertility
(iii) a cessation of oestrus cycles due to the lack of oestrogens,
(iv) regression of the reproductive tract
(v) abortion due to regression of the corpus luteum
(b) in the male:
A suppression of production of testosterone from the Leydig cells in the testes resulting in lowered peripheral blood serum levels of circulating androgens, causes:
(i) reduced libido,
(ii) regression of the accessory sex glands, and
(iii) diminution in the testicular volume and reduction/cessation of spermatogenesis.

Antibodies against LHRH can be produced in a number of species by chemically conjugating LHRH to a suitable carrier and administering it in the presence of an appropriate adjuvant (Carrelli C. et al, 1982, Proc. Natl. Acad. Sci USA 79 5392–5395). Chemical conjugation is however, difficult to control and often results in a heterogeneous and ill-defined product. Moreover, an oil-based adjuvant is usually required for effective immunisation and this often leads to the formation of unacceptable side effects such as inflammation and granulomatous tissue lesions.

It is desirable to provide a means for producing good titres of antibodies against LHRH without the need to use strong adjuvants.

The TraT protein (TraTp) is coded by the TraT gene. TraTp is an outer membrane lipo-protein produced by certain strains of E. coli and is responsible for the resistance of these strains to killing by serum. When injected intramuscularly into mice, without adjuvant, TraTp elicits an antibody response which is comparable to that obtained when it is injected with incomplete Freund's adjuvant. Furthermore, chemical coupling of an immunogen to TraTp followed by administration of the complex in saline to an animal results in the production of high levels of anti-immunogen antibodies. TraTp, therefore, can be used as a self-adjuvanting carrier of immunogens. This use of TraTp has been described previously in International Patent Application No. PCT/AU87/00107 (published as WO 87/06590), wherein both chemical and genetic linkage of TraTp to immunogen molecules was described. The specific fusions made and described in that specification relate to large proteins. On the other hand, LHRH is a short peptide which makes it inherently difficult to use as an immunogen without a suitable carrier. Furthermore, as there is little variation in the peptide between species, it is seen as a self-antigen by the immune system and is consequently recalcitrant to the stimulation of an immune response. Fusion proteins comprising LHRH sequences and LTB (the B subunit of the heat labile toxin produced by certain strains of E. coli) have been described (International Patent Application No. PCT/AU86/00135 published as WO86/06635). These constructs were prepared for the purpose of orally presenting LHRH to the immune system of a host, using the ability of LTB to bind to mucosal epithelium. They are not self-adjuvanting and although inhibition of reproductive function was demonstrated, the resulting inhibition was not a strong inhibition.

PCT/EP89/01013 (published as WO 90/02187) describes the production of fusion proteins including a peptide which alone is not substantially antigenic such as LHRH using a "carrier" which is a highly antigenic, hydrophilic protein such as hepatitis B surface antigen. TraTp is a membrane lipoprotein and is not a highly hydrophilic protein. Further the fusions taught in PCT/EP89/01013 do not appear to be self-adjuvanting.

| Abbreviations | |
|---|---|
| LHRH: | Luteinizing Hormone Releasing Hormone |
| LH: | Luteinizing Hormone |
| GnRH: | Gonadotrophin Releasing Hormone (is another name for LHRH) |
| FSH: | Follicle Stimulating Hormone |
| LTB: | The B subunit of the heat-labile toxin produced by certain strains of *E. coli* |
| QC: | Quality Control |
| QA: | Quality Assurance |
| EDTA: | Ethylene diaminetetra-acetic acid |
| SDS: | Sodium Dodecyl Sulphate |
| SDS-PAGE: | Sodium Dodecyl Sulphate Polyacrylamide gel electrophoresis |
| LPS: | Lipopolysacharide |
| EDAC: | 1-ethyl-3-(3-dimethyl-aminopropyl)-carbodiimide HCl |
| ABTS: | $2,2^1$-Azinobis(3-ethylbenzthiazoline sulphonic acid) |
| PEG: | Polyethylene glycol |
| BSA: | Bovine Serum Albumin |
| IF: | Insoluble form of the fusion protein |
| SF: | Soluble form of the fusion protein |
| PHA: | Phytohaemagglutinin |
| MBS: | m-maleimido benzoic acid n-hydroxysuccinimide ester |
| $A_{280}$: | Absorbance, at a setting of 280 nm on the spectrophotometer |
| ISA-20: | Montanide adjuvant, SEPPIC |
| ISA-25: | Montanide adjuvant, SEPPIC |
| sem: | Standard error of the Mean |
| sd; | Standard deviation |
| PBS: | Phosphate Buffered Saline, pH 7.2–7.4 |
| w/w: | Weight for weight |
| v/w: | Volume for weight |
| DNA: | Deoxyribonucleic acid |
| NSB: | Non-specific binding |

Definitions

TraTp refers to the protein product of the TraT gene.

TraTp-LHRH denotes a fusion protein formed as the expression product of a TraT and LHRH gene fusion.

TraTp-LHRH protein fusions are denoted as 730p, 731p etc., according to the plasmid which expressed them.

Plasmids are denoted as pBTA 730, etc.

*E. coli*/plasmid combinations are denoted as BTA 1664, etc.

TraTp analogues according to the present invention are molecules related to the TraTp SEQ ID NO. 12 sequence where alterations such as insertions, deletions or substitutions occur due to the strategy used for the fusion of LHRH analogue sequences to the TraTp sequences.

LHRH analogues according to the present invention are molecules related to the LHRH sequence where amino acid differences occur which take into account either variations in the above identified sequence which occur between species, variations in post-translational modifications to particular residues which occur because of particular fusion strategies or variations in amino acid sequence which occur because of particular fusion strategies.

DESCRIPTION OF THE INVENTION

In the present invention, particular insertion sites in TraTp have been identified which lead to the production of novel fusion proteins of TraTp or an analogue thereof and analogues of LHRH, capable of eliciting strong immune responses to LHRH. The present inventors have shown that not all fusions of LHRH analogues and TraTp or TraTp analogues are suitable for producing good titres of antibodies against LHRH. Further, between species variations were seen in the effect of different multimers of an LHRH analogue in a particular location in TraTp.

The present invention demonstrates that fusion of LHRH analogue coding sequences to TraTp or TraTp analogue coding sequences can be used to effectively provide vaccines useful in the inhibition or control of reproductive function in vertebrate hosts and particularly in domesticated animals.

According to the present invention recombinant DNA technology can be used to produce novel fusion proteins of TraTp or TraTp analogues and LHRH analogues which, when administered in saline or an adjuvant such as saponin lead to the production of antibodies which recognise LHRH (referred to hereafter as LHRH antibodies) which, in turn, inhibit reproductive functions in animals.

Work with immunogenic fusions exemplified herein shows that insertion of tandem repeats of LHRH analogues gives a more immunogenic fusion than the insertion of a single insert.

Advantages associated with making the fusion proteins in *E. coli* compared with chemical conjugation of TraTp and LHRH include:

a) the production process is simpler than that for chemical conjugation;

b) it is easier to define the nature of a fusion protein product than that of a chemical conjugate, thus giving product quality control (QC) and production quality assurance (QA) advantages; and c) fusions provide greater specificity and flexibility than chemical conjugation because the exact position of insertion of the LHRH analogue into TraTp or a TraTp analogue can be selected and the number of repeating epitopes can be chosen to give the optimum immunological response.

The invention provides novel fusion proteins. These fusion proteins may comprise a single copy of an analogue of the LHRH decapeptide inserted into or fused to TraTp or an analogue thereof or may comprise multiple copies of LHRH analogue which may be inserted at multiple locations within TraTp or the TraTp analogue. Particular cloning strategies may necessitate the inclusion of nucleotides coding for sequences which are not native to LHRH, the analogue or TraTp, or may lead to the deletion of bases from coding sequences.

Preferably, the fusion comprises the LHRH analogue (Sequence ID NO: 2)

Preferably, the at least one LHRH analogue is inserted between amino acids 80 and 81, 200 and 201 or 235 and 236 of the TraTp sequence, or in a combination of these sites where amino acid 1 is the Met 1 of the TraTp signal sequence.

The novel fusion proteins of the invention can be utilised to provide vaccines suitable for administration to domestic animals to inhibit or modify reproductive function in those animals.

The present invention also provides a polynucleotide molecule which encodes a fusion protein of the invention.

Preferred polynucleotide molecules are recombinant DNA molecules. More preferably, the recombinant DNA molecules comprise plasmid vectors. A preferred vector is pBTA 812. It will be recognised that vectors other than plasmid vectors could be used. Other vectors include other expression systems including viral, cosmid and phasmid vectors.

The invention further provides a transformant host carrying a polynucleotide molecule of the invention. Typically, the host is a bacterial host such as *E. coli*. A preferred host is *E. coli* strain N 4830 which is used in conjunction with a polynucleotide molecule of the invention wherein the fusion gene is under control of the $P_L$ promoter. Other hosts which could be used include yeasts, fungi, other bacterial hosts and other eukaryotic hosts including insect and mammalian cell lines.

The vaccines of the invention comprise at least one fusion protein of the invention together with a carrier, diluent, excipient and/or adjuvant suitable for human or veterinary use.

The amount of fusion protein that may be combined with carrier to produce a single dosage form will vary depending upon the condition being induced, the host to be treated and the particular mode of administration.

It will be understood, also, that the specific dose level for any particular host will depend upon a variety of factors including the activity of the specific fusion protein, the age, body weight, general health, sex and diet of the host, time of administration, route of administration, rate of excretion, and drug combination.

The vaccines of the present invention may be administered orally, parenterally, rectally or vaginally in dosage unit formulations containing conventional, non-toxic, pharmaceutically acceptable carriers, diluents, adjuvants and/or excipients as desired.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as solvent or suspending medium. For this purpose any bland fixed oil may be employed including synthetic mono- or di-glycerides. In addition, fatty acids such as oleic acid find use in the preparation of injectables.

Suitable adjuvants for the vaccination of animals or humans include but are not limited to saponin, oil emulsions such as Montanide ISA-20 or Montanide ISA-25, Marcol 52: Montanide 888 (Marcol is a Trademark of Esso. Montanide, Montanide ISA-20 and Montanide ISA-25 are Trademarks of SEPPIC, Paris), squalane or squalene, Adjuvant 65 (containing peanut oil, mannide monooleate and aluminium monosterarate), mineral gels such as aluminium hydroxide, aluminium phosphate, calcium phosphate and alum, surfactants such as hexadecylamine, octadecylamine, lysolecithin, dimethyldioctadecylammonium bromide, N,N-dioctadecyl-N', N'-bis(2-hydroxyethyl) propanediamine, methoxyhexadecylglycerol and pluronic polyols, polyanions such as pyran, dextran sulfate, DEAE-dextran, polyacrylic acid and carbopol, peptides and amino acids such as muramyl dipeptide, dimethylglycine, tuftsin and trehalose dimycolate. The fusion proteins of the present invention can also be administered following incorporation into liposomes or other micro-carriers, or after conjugation to polysaccharides, proteins or polymers or in combination with Quil-A to form "Iscoms" (Immunostimulating complexes) (Morein et al., Nature 308, 457–460[1984]).

Routes of administration, dosages to be administered as well as frequency of injections are all factors which can be optimized using ordinary skill in the art. Typically, the initial vaccination is followed some weeks later by one or more "booster" vaccinations, the net effect of which is the production of high titres of antibodies against the immunogen.

Suppositories for rectal or vaginal administration of the fusion proteins of the invention can be prepared by mixing the fusion protein with a suitable nonirritating excipient such as cocoa butter, theobroma oil, glycerinated gelatin or polyethylene glycols which are solid at ordinary temperatures but liquid at rectal or vaginal temperature or by contact with fluids present in the appropriate cavity and will therefore melt in the rectum or vagina and release the fusion protein.

Solid dosage forms for oral administration may include capsules, tablets, pills, powders, and granules. In such solid dosage forms, fusion proteins may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include nanoparticles, microcapsules, in pharmaceutically acceptable emulsions, syrups, solutions, suspensions, and elixirs containing inert diluents commonly used in the art, such as water. Such compositions may also comprise adjuvants, such as wetting agents, emulsifying and suspending agents and sweetening, flavouring, and perfuming agents including sugars such as sucrose, sorbitol, fructose etc, glycols such as polyethylene glycol, propylene glycol etc, oils such as sesame oil, olive oil, soybean oil etc, antiseptics such as alkylparahydroxybenzoate etc, and flavours such as strawberry flavour, peppermint etc.

The invention further provides a method of controlling reproductive function in a vertebrate host which is preferably a domestic animal which method comprises administering a fusion protein or a vaccine of the invention to the host to vaccinate the host.

The invention also provides a method for inhibiting reproductive function in a vertebrate host which is preferably a domestic animal which method comprises administering a fusion protein or vaccine according to the invention to the host, to vaccinate the host. The fusion proteins of this invention, therefore have application in the control of fertility and reproductive cyclicity of vertebrates generally, but in particular the control of mammalian reproductive activity in pet animals such as the dog and cat and in animals used for commercial purposes such as cattle, sheep, goats, pigs, horses, etc. Fusion proteins of the invention are typically synthesised in *E. coli* following the expression of a chimeric gene coding for TraTp or a TraTp analogue and an LHRH analogue.

There are several possible strategies by which such chimeric genes may be made. These include but are not limited to:

1. Random insertion: Using appropriate gene construction techniques, LHRH analogues may be positioned anywhere within the TraT protein or an analogue thereof. The product can be tested for anti-LHRH immunogenicity and the best construct selected as the basis of a vaccine. There are a number of possible methods.

a) DNA coding for TraTp or an analogue thereof may be subjected to random cleavage using DNAse I [Lin et al Anal. Biochem. 197, 114–119 (1985)], a DNA fragment coding for an LHRH analogue is inserted and the resulting plasmid cloned into *E. coli*. By placing the TraT gene under the control of a suitable promoter, induction will result in a proportion of the recombinant clones expressing fusions which can be selected by colony immunoassay with LHRH antibodies for further characterisation.

b) by insertion of LHRH analogue encoding DNA at convenient restriction sites in the TraT gene. The DNA insert should be tailored to be compatible with the various cohesive termini produced by different restriction endonucleases and should retain the translational reading frame.

2. Directed insertion: Insertion of an LHRH analogue within the TraTp or TraTp analogue sequence such that it is exposed on the surface of the TraTp or TraTp analogue may cause minimal disruption of TraTp or the analogue and result in optimal presentation of the LHRH analogue to the immune system by mimicking TraTp-LHRH conjugations in which LHRH is preferably located on the outer surface of the molecule. An alternative approach would be to replace part of the TraTp with an LHRH analogue. This directed insertion is performed by construction of suitable restriction enzyme sites at specific locations in the gene sequence.

3. An LHRH analogue may be inserted as a monomer at one site in TraTp or a TraTp analogue; as a monomer at more than one site or as multiple copies at one or more sites.

4. Analogues of LHRH, containing amino acid substitutions, insertions or deletions at one or more sites, may be used in any of the above means. It must be noted that the amino-terminal pyroGlu of LHRH cannot be formed when the amino acid sequence encoded by an LHRH gene is within a fusion protein. Therefore expression of the gene results in a Glu-1 analogue of LHRH within the TraTp protein. Similarly, the carboxy-terminus of the native molecule is a glycinamide residue as a result of post-translational processing. When the amino acid sequence coding for LHRH is positioned in a fusion such that this is an internal residue post-translational processing will not occur and therefore a Gly-10 analogue of LHRH results.

Other useful analogues include but are not limited to;

(a) naturally occurring variants of LHRH such as: (Sequence ID NO: 3) chicken II: (SEQ ID NO. 54) pyroGlu-His-Trp-Ser-His-Gly-Trp-Tyr-Pro-Gly-$NH_2$; Salmon (SEQ ID NO: 5): pyroGlu-His-Trp-Ser-Tyr-Gly-Trp-Leu-Pro-Gly-$NH_2$;

(b) Glu-1, His-1, Pro-1 and Lys-6 analogues. (SEQ ID NO. 6, 7, 8, and 9)

BRIEF DESCRIPTION OF THE DRAWINGS

FIGS. 1A: Map of the plasmid pBTA 812 that expresses the TraT gene.

FIG. 1B. Sequence of the $P_L$ promoter and the 5' untranslated region of the TraT gene (Sequence ID NO. 10).

FIGS. 2A and 2B: Coding sequence of TraT (SEQ ID NO: 11) and derived peptide sequence of TraTp (Sequence ID NO: 12) Numbers below each line refer to the amino acids. Restriction sites used for the insertion of the LHRH analogue coding sequence are shown.

FIGS. 3A and 3B: DNA and amino acid sequence of TraTp-LHRH fusion proteins pBTA 609 (SEQ ID NOS. 13 and 14), pBTA 732 (SEQ ID NOS. 15 and 16), pBTA 735 (SEQ ID NOS. 17 and 18), pBTA 737 (SEQ ID NOS. 19 and 20), pBTA 734 (SEQ ID NOS. 21 and 22), pBTA 733 (SEQ ID NOS. 23 and 24), pBTA 731 (SEQ ID NOS. 25 and 26), pBTA 740 (SEQ ID NOS. 27 and 28), and pBTA 730 (SEQ ID NOS. 29 and 30). Only the LHRH analogue and the neighbouring TraTp sequence is shown for each construct. Numbers refer to the amino acids in TraTp.

FIGS. 4A and 4B: FIG. 4A Sequence of DNA fragments coding for LHRH analogue (Sequence ID NO: 31, 33 and 32)

FIG. 4B Sequence of linker DNA (Sequence ID NO. 34 and 35)

FIG. 4C Sequence of LHRH analogue DNA (Sequence ID NO: 35, 38and 37) used in the construction of pBTA 870

FIG. 4D Sequence of LHRH analogue dimer DNA (Sequence ID NO. 39, 41 and 40) used in the construction of pBTA 862.

FIGS 5A and 5B: Sequence of multimeric inserts pBTA 870 (SEQ ID NOS. 42 and 43), pBTA 862 (SEQ ID NOS. 44 and 45), and pBTA 859 (SEQ ID NOS. 46 and 47) of LHRH analogue in TraTp. The numbers denote amino acids in TraTp, as in FIGS. 2A and 2B.

FIG. 6: Proliferative responses of T-cells from dogs immunised with 732p in various formulations. Data are presented as the mean±sd. Stimulation index, was calculated by dividing the c.p.m. in the presence of antigen, by c.p.m. in the absence of antigen.

FIG. 7: The mean (±sem) LHRH serum antibody response from dogs immunised on Days 0,28 & 56, with 732p in various formulations. Blood samples (5–8 ml) were collected from the cephalic or jugular veins on Days 0, 28, 42, 56 & 70 and the sera were (at dilution of 1:2000 final) analyzed for their ability to bind $^{125}$I-LHRH in an LHRH tracer binding assay (described in Example 38).

FIG. 8: The mean (±sem) LHRH serum antibody response from dogs immunised on Days 0,28 & 56, with 732p and Day 121 with TraTp-LHRH fusion protein, 862p containing four inserts of LHRH analogue arranged in tandem (also set forth in Sequence ID NO. 30). Each dog received 500μg of 862p in 0.05% saponin and 0.1% SDS. These dogs were bled on Days 121 (prior to booster #3), 134, 141, 155, 162, 164 and 167 and the sera were analyzed for their ability to bind $^{125}$I-LHRH in an LHRH tracer binding assay (described in Example 3B).

FIGS. 9A and 9B: The mean (±sem) LHRH serum antibody response was determined on Days 28 and 42, from FIGS. 9A dogs and, FIG. 9B mice, immunised on Days 0 & 28 with TraTp-LHRH analogue fusion proteins, 733p, 870p, 862p, 859p. Sera (at dilution of 1:2000 final) were analyzed for their ability to bind $^{125}$I-LHRH in an LHRH tracer binding assay (described in Example 3B).

FIG. 10: Serum testosterone concentrations (ng/ml; described in Example 3C) and, LHRH serum antibody binding in dog #060/10. Blood was taken on Days 0, 28, 42, 56, 70, 84 (immunised, with 732p; 1000μg) and 121 (boosting with 862p; 500μg), 134, 141, 148, 155, 162, 169 and 176. Days are with respect to the primary immunisation with 732p (at Day 0). Sera (at dilution of 1:2000 final) were analyzed for their ability to bind $^{125}$I-LHRH in an LHRH tracer binding assay (described in Example 3B).

Figure 11:
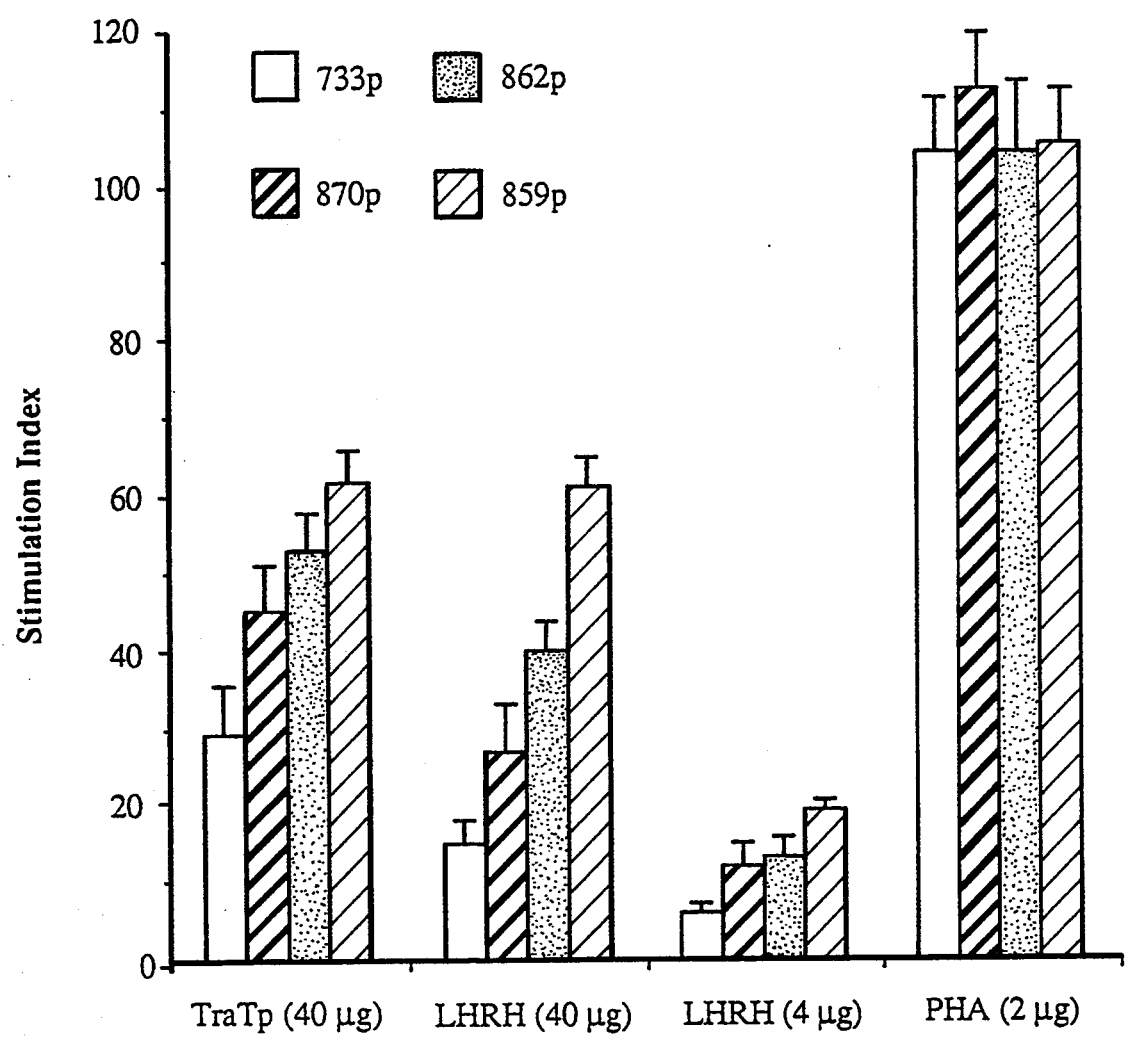

FIG. 11: Proliferative response of T-cells from dogs immunised with various TraTp-LHRH analogue fusion proteins in a saponin/SDS adjuvant. Data are presented as the mean ±sd. Stimulation index, was calculated by dividing the c.p.m. in the presence of antigen, by c.p.m in the absence of antigen.

BEST MODE OF CARRYING OUT THE INVENTION

The recombinant DNA molecules and transformant hosts of the invention are prepared using standard manipulations of molecular biology, such as digestion, ligation etc.

Fusion proteins of the invention are obtained by culturing the transformant hosts of the invention under standard conditions as appropriate to the particular host and separating the fusion protein from the culture by standard techniques. The fusion protein may be used in impure form or may be purified by standard techniques as appropriate to the fusion protein being produced.

The vaccines of the invention are prepared by mixing, preferably homogeneously mixing, fusion protein with a carrier, diluent, excipient and/or adjuvant acceptable for human or veterinary use using standard methods of pharmaceutical preparation.

The amount of fusion protein required to produce a single dosage form will vary depending upon the condition to be induced, host to be treated and the particular mode of administration. The specific dose level for any particular individual will depend upon a variety of factors including the activity of the fusion protein employed, the age, body weight, general health, sex, and diet of the individual, time of administration, route of administration, rate of excretion and drug combination.

The vaccine may be administered orally, parenterally, rectally or vaginally in unit dosage formulations containing conventional, non-toxic, carriers, diluents, excipients and/or adjuvants acceptable for human or veterinary use as desired.

The invention is further described with reference to the following Examples which are in no way limiting on the scope of the invention.

EXAMPLE 1.

PLASMIDS WHICH EXPRESS VARIOUS TraT-LHRH ANALOGUE FUSION PROTEINS.

The TraTp-LHRH analogue fusion proteins are produced in *E. coli*. The gene coding for TraTp is carried on a multicopy plasmid vector which has been modified by the insertion of one or more copies of DNA coding for an LHRH analogue. Where the LHRH gene is the 5' end of the fusion, a pyroGlu containing fusion protein may result but where the LHRH gene is within TraT sequences a TraTp LHRH fusion protein containing Glu-1 as the first amino acid in the LHRH sequence is produced. Similarly, where LHRH is the 3' end of the fusion a glycinamide containing fusion protein may result but where the LHRH gene is within TraT sequences a TraTp-LHRH analogue fusion protein containing Gly-10 as the last amino acid in the LHRH sequence is produced.

The basic TraT expression vector pBTA 812 is illustrated in FIG. 1A. It is derived from plasmid pBR322 [Bolivar F. et al (1977) Gene 2 95–113] and carries an ampicillin resistance gene which permits selection of plasmid bearing *E. coli*. (Alternative selectable genes could be incorporated such as those coding for other antibiotic resistance.) It also carries the leftward promoter ($P_L$) of lambda which promotes the transcription of the TraT gene [Ogata R. T. et al. (1982) J. Bacteriol. 151 819–827]. Plasmid BTA 812 is similar to pBTA 439 which was described in PCT/AU87/00107 (published as WO87/06590) and was deposited with the American Type Culture Collection as ATCC 67331. pBTA 812 can be made as follows. $pP_L$-lambda (plasmid and sequence provided by Pharmacia LKB, Uppsala, Sweden) is digested with restriction endonucleases SmaI and EcoRI according to the manufacturers instructions and the linear vector religated in the presence of DNA polymerase I (Klenow fragment) and deoxynucleotide triphosphates. (Methodology is as described by T. Maniatis, E. F. Fritsch and J. Sambrook in "Molecular Cloning: A Laboratory Manual", Cold Spring Harbor Laboratory Press, 1982). Each ligation step is followed by transformation of the product into a suitable *E. coli* host strain (e.g. C600λ which carries the repressor of the $P_L$ promoter). The new plasmid now lacks EcoRI, SmaI and one of the BamHI sites. This plasmid can then be cut with HpaI and treated with exonuclease such as Ba131 (Promega) to remove DNA coding for the N gene as well as most of the 5' untranslated N gene DNA, followed by phenol extraction and ethanol precipitation of the DNA. This is then cut with XmnI and DNA of approximately 670 base pairs isolated by electrophoresis on low gelling temperature agarose gels. pBTA439 is cut with SmaI and SacI then religated in the presence of Klenow fragment and deoxynucleotide triphosphates (this removes these sites) followed by cutting with BamHI and BglII and religation (to remove BamHI, SalI, PstI and BglII sites). The resulting plasmid is cut with EcoRI and XmnI and a 3052 base pair fragment isolated by electrophoresis on agarose gels and ligated to the 670 base pair fragment described above in the presence of Klenow fragment and deoxynucleotide triphosphates. Selection by growth on ampicillin ensures the correct orientation of the fragments due to the reconstitution of the β-lactamase gene. The EcoRI site is reconstituted when a G in the top strand of the approximately 670 base pair fragment is next to the AATTC of the 3054 base pair fragment. Recombinant plasmids are screened for the presence of an EcoRI site and the DNA of the positive clones is sequenced in the region of the EcoRI site. The sequence of the $P_L$ promoter and that corresponding to the 5' untranslated mRNA of pBTA812 is shown in FIG. 1B and in Sequence ID NO: 10.

The $P_L$ promoter and the expression of TraTp is controlled by the temperature sensitive repressor cI857 which is present in modified *E. coli* strains such as N4830 [see M. Joyce and NDF Grindley (1983) Proc. Natl. Acad. Sci. USA 80 1830–1834].

The full coding sequence of TraTp (SEQ ID NO: 12) is shown in FIG. 2A and 2B (Ogata op. cit.) and in Sequence ID NO: 11. This includes the signal sequence which may be cleaved in *E. coli* between amino acids 20 and 21 to leave an N-terminal cysteine which carries a fatty acid modification [Perumal, N. B. and Minkley E. G. (1984) J. Biol. Chem. 259 5359–5360].

Restriction sites within the TraT gene which have been used as sites of insertion of the LHRH analogue DNA are indicated.

Examples of 8 plasmid constructs which express TraTp-LHRH analogue fusions are illustrated in FIGS. 3A and 3B and SEQ ID NOS. 13–30. The unique insertion positions were distributed over the whole of the TraTp molecule.

Plasmid construction; pBTA 812 was prepared by extraction from a suitable E. coli K12 host strain (e.g. C600λ) and purification on caesium chloride density gradients.

pBTA 731 (SEQ. ID NOS. 25 and 26) was constructed by cutting pBTA 812 with restriction endonuclease HpaI according to manufacturer's instructions and purifying the linear DNA, for example on low gelling temperature agarose (Maniatis op. cit).

DNA coding for LHRH analogue as shown in FIG. 4A Sequence ID NOS. 31, 33, and 32 was synthesized by a method based on that described by Beaucage S. L. and Caruthers (1981) Tetrahedron Lett. 22 1859–1862, ligated to the linearised pBTA 812 and transformed into a suitable strain of E. coli K12. Plasmid containing cells are selected by plating onto media containing ampicillin. Colonies with plasmids which have the LHRH analogue insert were identified either by colony hybridisation using [$^{32}$P]-labelled LHRH DNA as a probe (Maniatis op. cit.) or by picking a number of colonies, extracting the plasmid and determining the presence of a SmaI restriction site which is unique to the LHRH DNA. The correct sequence and orientation of the LHRH analogue DNA and neighbouring TraT DNA was confirmed by dideoxy nucleotide sequencing.

pBTA 730 (SEQ ID NOS. 15 and 16), 733 (SEQ ID NOS. 23 and 24) and 734 (SEQ ID NOS. 21 and 22) were constructed by digesting pBTA 812 with limiting amounts of restriction endonuclease SspI, ScaI and RsaI respectively such that not all of the sites for those enzymes in the plasmid were cut. Only the plasmid which was cut once with each enzyme was removed from the low gelling temperature agarose gel following electrophoresis. DNA coding for LHRH analogue as shown in FIG. 4A and in Sequence ID NOS: 31, 33, and 32 was ligated into this DNA and E. coli carrying the appropriate new recombinant plasmids were identified as described above. Restriction mapping and DNA sequencing was used to show that the correct restriction site contained LHRH analogue DNA in the correct orientation.

pBTA 732 (SEQ ID NOS. 15 and 16), 735 (SEQ ID NOS. 17 and 18), 737 (SEQ ID NOS. 19 and 20) and 740 (SEQ ID NOS. 27 and 28): these required the construction of intermediates which contain a short linker fragment of DNA inserted at the chosen site. The linker and (FIG. 4B Sequence ID NO: 34 and 35) provides a unique new SmaI site located between codons such that the DNA coding for LHRH analogue can be inserted in frame for expression of TraTp-LHRH analogue full length fusion proteins.

pBTA 812 was cut to completion with either restriction endonuclease EcoRV, StuI or BalI or partially with HaeIII and linear DNA which has been cut once with each of these enzymes isolated by agarose gel electrophoresis. Linker DNA (FIG. 4B Sequence ID NO: 34 and 35) was ligated into each of these DNAs and inserted into E. coli. Recombinants were screened by colony hybridisation (using radioactively labelled linker as a probe or by restriction analysis of the DNA from a number of colonies). The linker had been designed such that the SmaI site will be situated between codons depending on the orientation of the linker. The orientation of the linker was determined either by sequencing the DNA in that region or by the presence of a new restriction site when this was created or by inserting the LHRH analogue gene in the SmaI site and assaying the recombinants for the expression of a TraTp-LHRH analogue fusion protein.

The DNA coding for (FIG. 4A an LHRH analogue in Sequence ID NOS. 31, 33, and 32) was inserted into the SmaI site of the constructs containing the linkers as described for pBTA 730 above. On determining the nucleotide sequence of the final constructs pBTA 732 (SEQ ID NOS. 15 and 16) was found to have lost three bases at the 3′ junction of the LHRH analogue/linker/-TraT DNA.

pBTA 609 (SEQ ID NOS. 13 and 14) is a TraTp-LHRH analogue fusion in which the LHRH analogue has been inserted between amino acids 31 and 32. The codons were converted to a PvuII site by in vitro mutagenesis (the new codons represent Gln and Leu) and the DNA coding for LHRH analogue was inserted into this site. This position was chosen because the protein sequence is particularly hydrophilic in this region. An inserted peptide in this position may be exposed on the surface of the TraTp molecule and may therefore be more antigenic.

pBTA 736 (host vector combination BTA 1669) contains LHRH analogue inserted at two different sites in TraT and is a composite of pBTA 731 (SEQ ID NOS. 25 and 26) and pBTA 732 (SEQ ID NOS. 15 and 16).

Plasmids were also constructed which contained multiple insertions of LHRH analogue at single positions. The construct with two LHRH analogue molecules (pBTA 870) (SEQ ID NOS. 42 and 43) was made by inserting the DNA coding for LHRH analogue as shown in FIG. 4C (Sequence ID NOS. 36, 38 and 37) into the SmaI site of the LHRH analogue in pBTA 733 (SEQ ID NOS. 23 and 24) and, after transformation, identifying colonies with two LHRH analogue inserts as described above. The original SmaI site was not reconstituted but the new LHRH analogue insert carried a SmaI site in the equivalent position in the second LHRH analogue gene (FIGS. 5A and 5B; pBTA 870 (Sequence ID NOS. 42 and 43)).

A further construct with four LHRH analogue repeats (pBTA 862(Sequence ID NOS. 44 and 45)) was made by inserting DNA coding for a dimer of LHRH analogue (FIG. 4D (Sequence ID NOS. 39, 41 and 40)) into the SmaI site of pBTA 870 (SEQ ID NOS. 42 and 47). Again, the original SmaI site was lost and a new SmaI site created near the end of the LHRH analogue DNA. Constructs with six and eight repeats of LHRH analogue were made by successive additions of the LHRH analogue dimer DNA to pBTA 862 (SEQ ID NOS. 44 and 45). The DNA sequence of some of the LHRH analogue genes was varied (making use of codon degeneracy) to avoid plasmid instability which might occur when using multiple identical tandem repeats of DNA.

FIG. 5A and 5B illustrate plasmids pBTA 870 (SEQ ID NOS. 42 and 43), pBTA 862 (SEQ ID NOS. 44 and 45), pBTA 859 (SEQ ID NOS. 46 and 47) which carry two, four and eight LHRH analogue insertions respectively (and as set forth in Sequence ID NO: 29, 30 and 31 respectively) between amino acids 200 and 201 of TraTp (SEQ ID NOS: 12). It can be seen that plasmids similar to pBTA 870, pBTA 862 and pBTA 859 containing multiples of LHRH analogue DNA could be constructed using as starting plasmids pBTA 732 (SEQ ID NOS. 15 and 16) and pBTA 740 (SEQ ID NOS. 27 and 28).

All the above plasmids were inserted into *E. coli* strains containing the temperature sensitive repressor cI857 [M. Joyce, N. D. F. Grindley, op. cit.] available from Pharmacia LKB, Uppsala, Sweden. Other strains carrying the CI857 repressor might be used instead of N4830. Expression of the TraT-LHRH analogue genes is induced by raising the temperature of the plasmid-bearing *E. coli* culture from 28° C. to between 37° C. and 42° C. Each of the constructs produced a TraTp-LHRH analogue protein of the expected sizes. The production levels of each varied with the position of LHRH analogue insertion: most were produced at a higher level than TraTp alone. Following cell breakage, the fusion proteins were extracted and purified for injection into animals as in Example 2.

EXAMPLE 2:

PURIFICATION OF TraTp.-LHRH ANALOGUE FUSION PROTEINS

For the initial screening experiment described in Example 4, a simple fractionation procedure was used to separate the fusion proteins from the bulk of *E. coli* proteins. The *E. coli* strains containing the TraTp-LHRH analogue gene fusion plasmids were grown in shake flasks at 30° C. and induced at 41° C. for 3 hours. Bacteria were harvested by centrifugation (17,000g. for 20 min) and the cells lysed in 0.1M Tris-HCl pH7.5, 10mM EDTA using a French Press. Lysed cells were then separated from inclusion bodies by layering onto 25% glycerol and centrifuging for 15 min at $10,000 \times g$. Inclusion bodies (pellet) were suspended by sonication into 0.1M Tris-HCl pH 7.5, 50 mM EDTA containing 5% TRITON-X-100. The sonicated material was centrifuged for 20 min at $12,000 \times g$ to give an insoluble form (IF). A soluble form (SF) was obtained by resuspending the pellet in 0.1M Tris pH 7.5, 10 mM EDTA and 2% SDS. This material was then precipitated with ethanol to 50% and resuspended in saline (SF) prior to injection. The insoluble form (IF) was also suspended in saline prior to injection.

For later trials requiring larger quantities of immunogen of greater purity, the *E. coli* strains containing the TraTp-LHRH analogue gene fusion plasmids were grown in shake flasks at 30° C. and induced at 41° C. for 3h. Bacteria were harvested by centrifugation (17,000 g, for 20 min) and the cells lysed in 0.1M Tris-HCl pH 7.5, 50 mM EDTA using an APV Gaulin 15 MR homgenizer (7 passes at 9,000 psi). Following centrifugation (20 min, $10\,000 \times g$), the insoluble pellet fraction containing the fusion protein was washed once with lysis buffer and the protein then solubilized in 10% SDS, 0.1M Tris-HCl pH 7.5, 25 mM EDTA. This material was centrifuged (20 min $\times$ 15 000g) and the supernatant applied to a Sephacryl S-200 HR column equilibrated in 2% SDS, 50 mM Tris-HCl pH 7.5, 25 mM EDTA. The column was eluted with this buffer and fractions containing the fusion protein (analysed by SDS-PAGE) are precipitated with 50% ethanol. The pellet was extracted twice with 1% Zwittergent 3-12, 0.1M Tris-HCl pH 7.5, 25 mM EDTA, and then resolubilized in 2% SDS. This material was applied to a hydroxyapatite column equilibrated with 50 mM Na phosphate buffer pH 6.5, 0.5% SDS, and eluted with a 0.05–0.5M Na phosphate gradient pH 6.5 in 0.5% SDS. Fractions containing fusion protein were pooled and the purity analysed on SDS-PAGE. The protein concentration was determined by $A_{280}$ and amino acid analysis, and the lipopolysaccharide (LPS) content shown to be less than 1% (w/w). The final product was precipitated with 50% ethanol and resolubilized in 0.1% SDS prior to formulation.

EXAMPLE 3,

METHODS FOR DETERMINING ANTIBODY AND TESTOSTERONE PRODUCTION IN SERUM

A. ELISA "Immulon 2" microelisa plates (Dynatech) were incubated overnight at 4° C. with a 2μg/ml solution of ovalbumin-LHRH (prepared by EDAC conjugation) or 0.25μg/ml TraTp in 0.1M carbonate/bicarbonate pH 9.6 (100μl per well). After each step plates were washed 5 times with phosphate buffered saline containing 0.05% Tween (PBS/T). The plates were "blocked" with 200μl per well of 1% gelatine solution (Davis Gelatine Company Aust. Pry. Ltd.) in 0.1M carbonate/bicarbonate, for 1 hour at 37° C. The plates were washed as above. Sera were diluted 1:200 in PBS/T, and this was diluted two-fold in 100μl PBS/T. Sera were incubated for 1 hr at 37° C.

After washing in PBS/T, conjugates coupled to peroxidase were added to plates at 1/2000 in PBS/T (100 μl per well) and incubated at 37° C. for 40 to 45 minutes. The conjugates were Goat anti-rat IgG, (KPL) Rabbit anti-mouse IgG, (KPL), Rabbit anti-dog IgG (Nordic), Goat anti-bovine IgG (KPL) and Rabbit anti-sheep IgG (Dako).

After washing, 100μl of peroxidase substrate was added to each well. This substrate consisted of 0.5 mg/ml 2,2'-Azinobis (3-ethylbenzinthiazoline sulfonic acid) (ABTS) in 0.1M citrate phosphate buffer pH 4.0, to which 0.1% $H_2O_2$ was added immediately prior to addition to the plates. Unless otherwise stated, all chemicals and reagents used were of analytical grade from the Sigma Chemical Company.

B. LHRH TRACER BINDING ASSAY

Sera were diluted 1:500 in 0.01M phosphate buffered saline containing 0.5% w/v bovine serum albumin (PBS/BSA; referred to as buffer, below). One hundred microliters of this dilution was added to 3 ml polypropylene radioimmunoassay tubes (Johns) containing 200 μl of buffer. Added to this was 100 μl of 10,000 cpm, (approx.) of $I^{125}$ LHRH (Amersham/Dupont) giving a 1:2000 final dilution of the antiserum.

The tubes were incubated overnight at room temperature (14°–20° C). A second antibody (Sheep anti-mouse IgG or Sheep anti-dog IgG; Silenus); was diluted 1:20 with buffer, and added at 100 μl per tube, then incubated 1 hr at room temperature.

Polyethylene glycol (1 ml) 6000–7500 molecular weight (PEG,BDH) was added to each tube (except total counts), the tubes vortexed and then centrifuged for 30 minutes at 2,500 rpm. The supernatants were decanted and the tubes allowed to drain.

Pellets were counted in a multichannelled gamma counter (Clinigamma counter, LKB) for 1 minute. Results are expressed as a percentage (%) of total radioactive counts added [minus the non-specific binding (NSB)], to give a % of LHRH antibodies in the sera.

Unless otherwise stated, all chemicals and reagents used were of analytical grade from the Sigma Chemical Company.

C. MEASUREMENT OF TESTOSTERONE IN DOG SERUM

Testosterone was measured using a "Direct Testosterone commerical kit" (SPECTRIA, from Farmos Diagnostica, Finland), where the tubes supplied were pre-coated with second antibody. One hundred microliters of dog serum was added to the pre-coated tubes, in duplicate, followed by the addition of $^{125}$I-testosterone (200 μl), testosterone antiserum (200 μl; raised in rabbits) and incubated for exactly 2 h at 37° C. Castrate dog serum was added to the standard curve and QC's to compensate for any serum effects in the radioimmunoassay. Without centrifugation, the supernatants were decanted, tapped against absorbent paper, and washed with 1 ml of washing solution (phoshate buffer, supplied), allowed to drain, and subsequently counted in a multichannelled gamma counter (Clinigamma counter, LKB) for 1 minute. The data are presented as ng/ml of testosterone.

EXAMPLE 4.

IMMUNISATION OF MICE WITH TraTp-LHRH ANALOGUE FUSION PROTEINS

In order to determine which TraTp-LHRH analogue fusion protein was most active in eliciting LHRH antibodies, groups of female Swiss mice (n=5: 18–22 g each) were immunised with 9 different TraTp-LHRH analogue fusion protein constructs in the absence of adjuvant (730p to 737p and 740p) and both the insoluble (IF) and soluble (SF) forms of the protein were compared. Control groups (N=5) were immunised with TraTp prepared by the same methods.

Mice were injected with 150μg of protein in 100μl saline in each thigh muscle on Days 0 and 28.

Blood samples were collected from the retro-orbital plexus on Days 0, 28, and 42. Aliquots of sera from individual mice were pooled and analysed for LHRH antibody titre by ELISA and by an LHRH tracer binding assay. Data for bleeds on Day 42 are shown in Table 2.

The data show that only some of the fusion protein constructs, notably the proteins 732p, 733p and 740p were effective in raising LHRH antibodies when administered in saline. The sites for LHRH analogue insertion to generate an effective antigen could not have been predicted on inspection of the constructs made. Effective immunisation was achieved with both IF and SF materials from different constructs, assessed by determining the % binding to LHRH (& ELISA titres) and the concomitant effect on pregnancy (Table 2). The fusion proteins used in these experiments yield, single, well defined chemical entities which therefore have added advantages in stability, production, quality control and quality assurance compared to LHRH chemical conjugates.

EXAMPLE 5

T-CELL PROLIFERATIVE AND ANTIBODY RESPONSES IN DOGS IMMUNIZED WITH TraTp-LHRH ANALOGUE FUSION PROTEIN (732p) IN VARIOUS FORMULATIONS

This experiment was designed to determine whether the fusion protein 732p was capable of eliciting a T-cell, as well as an antibody response to LHRH in a target species such as the dog. A T-cell response may represent a desirable effector mechanism in the immune castration process itself and/or it may provide T-cell help in the production of LHRH antibodies.

Immunization of dogs with Fusion proteins and the measurement of T-cell proliferation and antibody response.

Fifteen dogs of mixed ages, sexes and breeds were randomly divided into three groups of five animals. One group received 1 mg of pBTA 732 fusion protein in alhydrogel, another group was given 1 mg of fusion protein in Montanide ISA-20 while the third group was injected with 1 mg of the fusion protein construct in saponin. All three formulations contained 0.1% SDS. Animals were injected intramuscularly on Days 0, 28 and 56.

A. T-cell Proliferation

The T-cell response following immunisation with the fusion protein derived from pBTA 732 was measured as follows. Briefly, blood samples (5–10ml) were collected from the cephalic or jugular veins (before the Day 42) and a T-cell-enriched cell fraction was prepared as follows. About 10 ml of heparinized blood was layered on 6 ml of Ficoll-Paque (Pharmacia) and T-cells were separated by gradient centrifugation at 400 g for 30–40 min. The yield of T-cells recovered from 10 ml of heparinized blood was between 15 to 20×10$^6$ T-cells (10$^5$ in 0.2 ml of RPMI 1640 medium (Flow Laboratories Inc., Mclean, Va, U.S.A.) containing 10% Fetal calf serum) were cultured in flat-bottom culture plates with varying amounts of TraTp, LHRH or PHA for 3 to 5 days at 37° C. Sixteen to eighteen hours before harvesting, cells were labelled with 0.5 μCi of tritiated thymidine, harvested and counted in a liquid Scintillation counter. Results are expressed as Stimulation indices, which are calculated by dividing the c.p.m. in the presence of antigen, by c.p.m. in the absence of antigen.

The data in FIG. 6 show that strong T-cell responses were elicited against both TraTp and LHRH in all three groups. The protein, 732p formulated in saponin appeared to be more effective in evoking T-cell responsiveness than in either Montanide ISA-20 or alhydrogel, particularly to LHRH. The strong T-cell responses obtained correlated reasonably well with the antibody responses to LHRH (as measured in a binding assay).

B. Antibody response

1. In order to determine the level of LHRH antibodies generated following immunisation with the fusion protein, 732p, blood samples (5–8 ml) were collected from the cephalic or jugular veins on Days 0, 28, 42, 56 & 70 and the sera (at dilution of 1:2000 final) analyzed for their ability to bind $^{125}$I-LHRH in an LHRH tracer binding assay (described in Example 3B).

Figure 7:
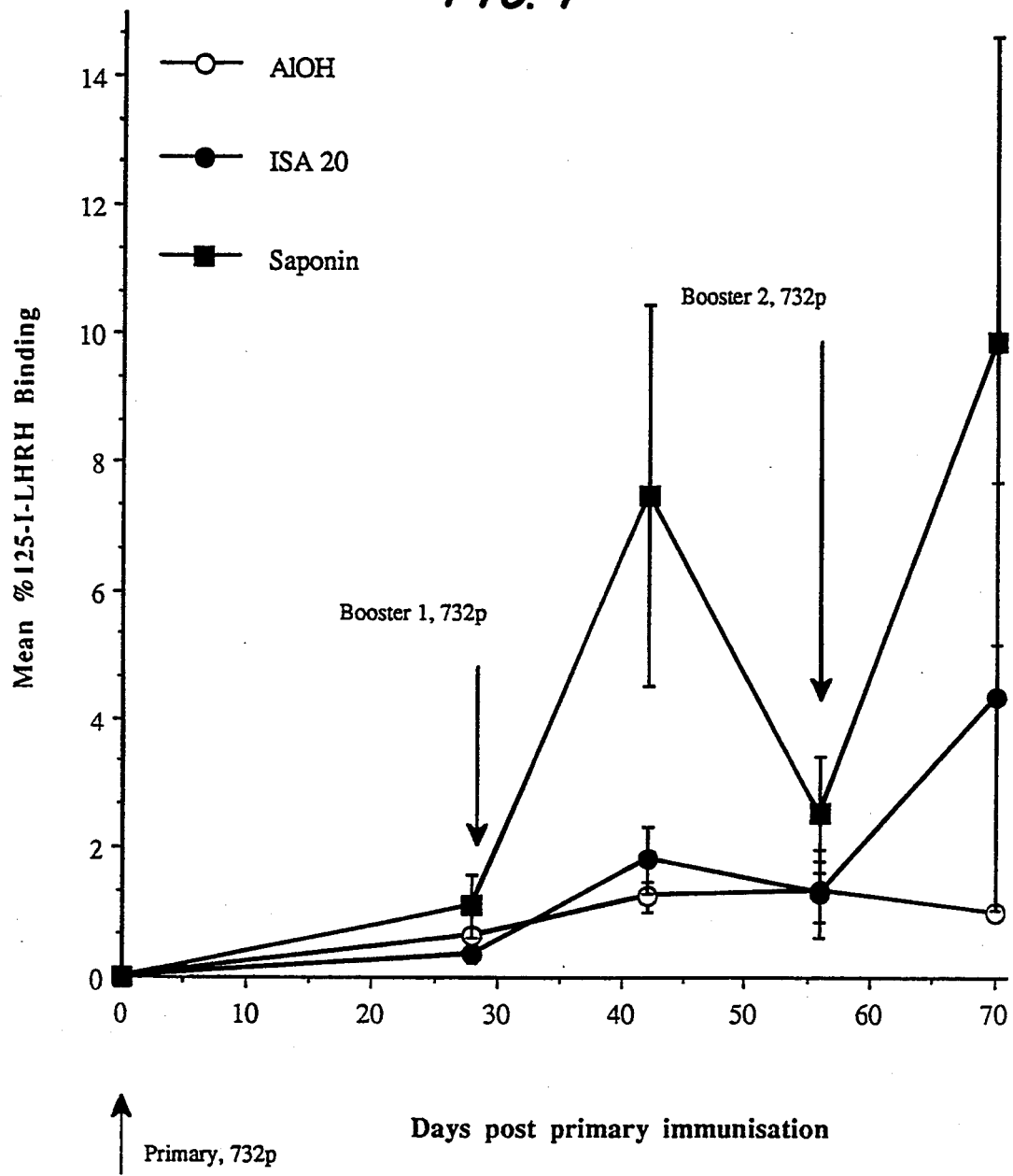

The data in FIG. 7 show that antibodies to LHRH were elicited in dogs that had been immunized with the 732p fusion protein in an SDS/Saponin formulation, while the anti-LHRH response was much lower in animals that had received the fusion protein in alhydrogel or Montanide ISA-20. It appears, therefore, that saponin is a more effective adjuvant for this fusion protein, than either alhydrogel or Montanide ISA-20, for eliciting antibodies to LHRH.

Figure 8:
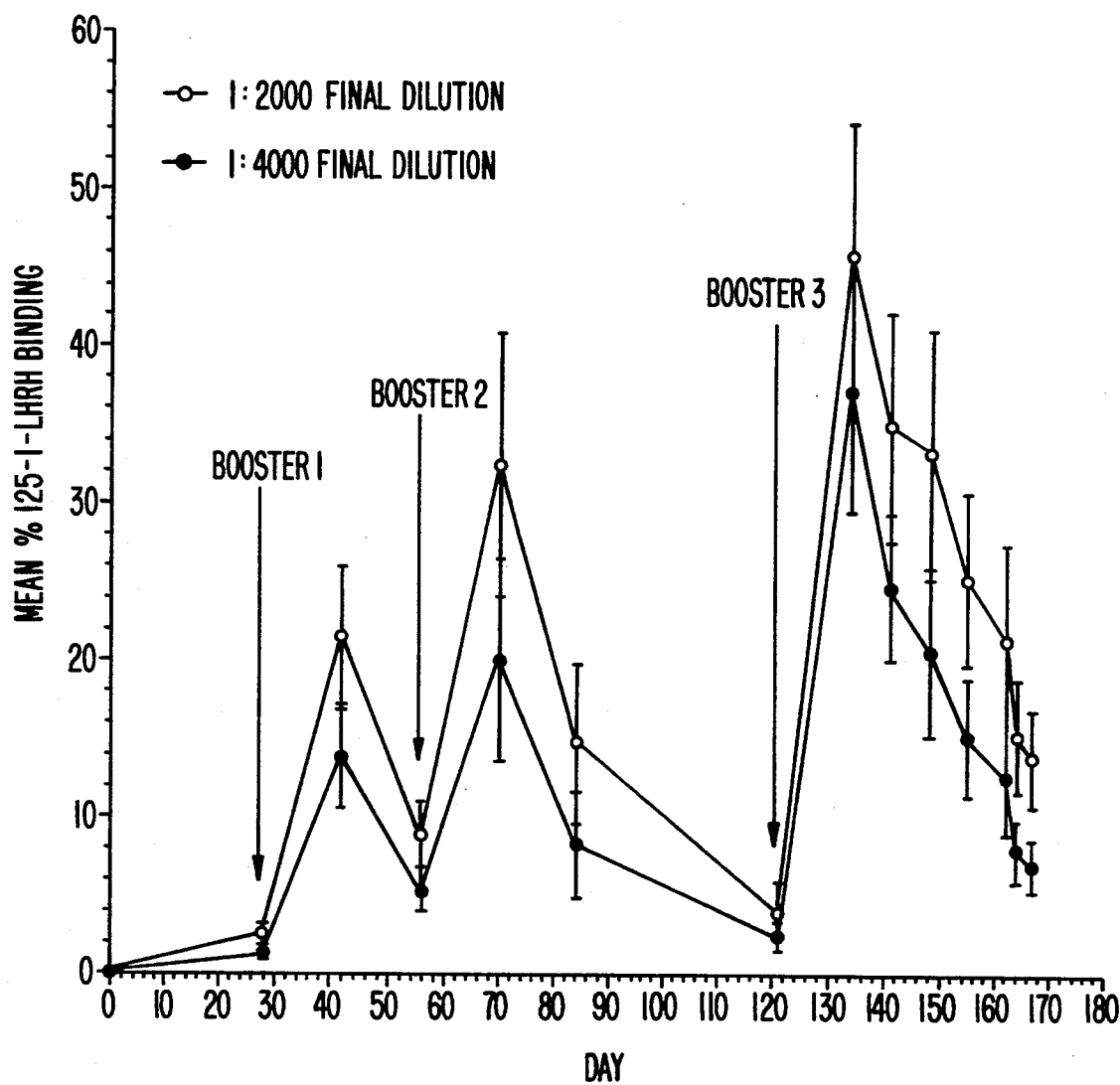

2. In order to assess the efficacy of a multi-LHRH analogue construct (862p) to stimulate LHRH antibodies, five dogs from the above experiment, four from the "Saponin group" and one from the Montanide ISA-20 group, were tested further as follows: on Day 121 (with respect to the primary immunisation) all five dogs received a further booster injection (booster #3 in FIG. 8) of a TraTp-LHRH analogue fusion protein (862p) containing four inserts of LHRH analogue arranged in tandem (Sequence ID NOS. 44 and 45); each dog received 500 μg of this fusion protein construct in 0.05% saponin and 0.1% SDS. These dogs were bled on Days 121 (prior to booster #3), 134, 141, 148, 155, 162, 164 and 167. The data in FIG. 8 show that high levels of LHRH antibodies were elicited in these five dogs in response to a TraTp fusion protein construct containing four inserts of LHRH analogue. The LHRH antibody response to 732p (booster 1 and booster 2 in FIG. 8) are also shown by way of comparison.

Figure 10:
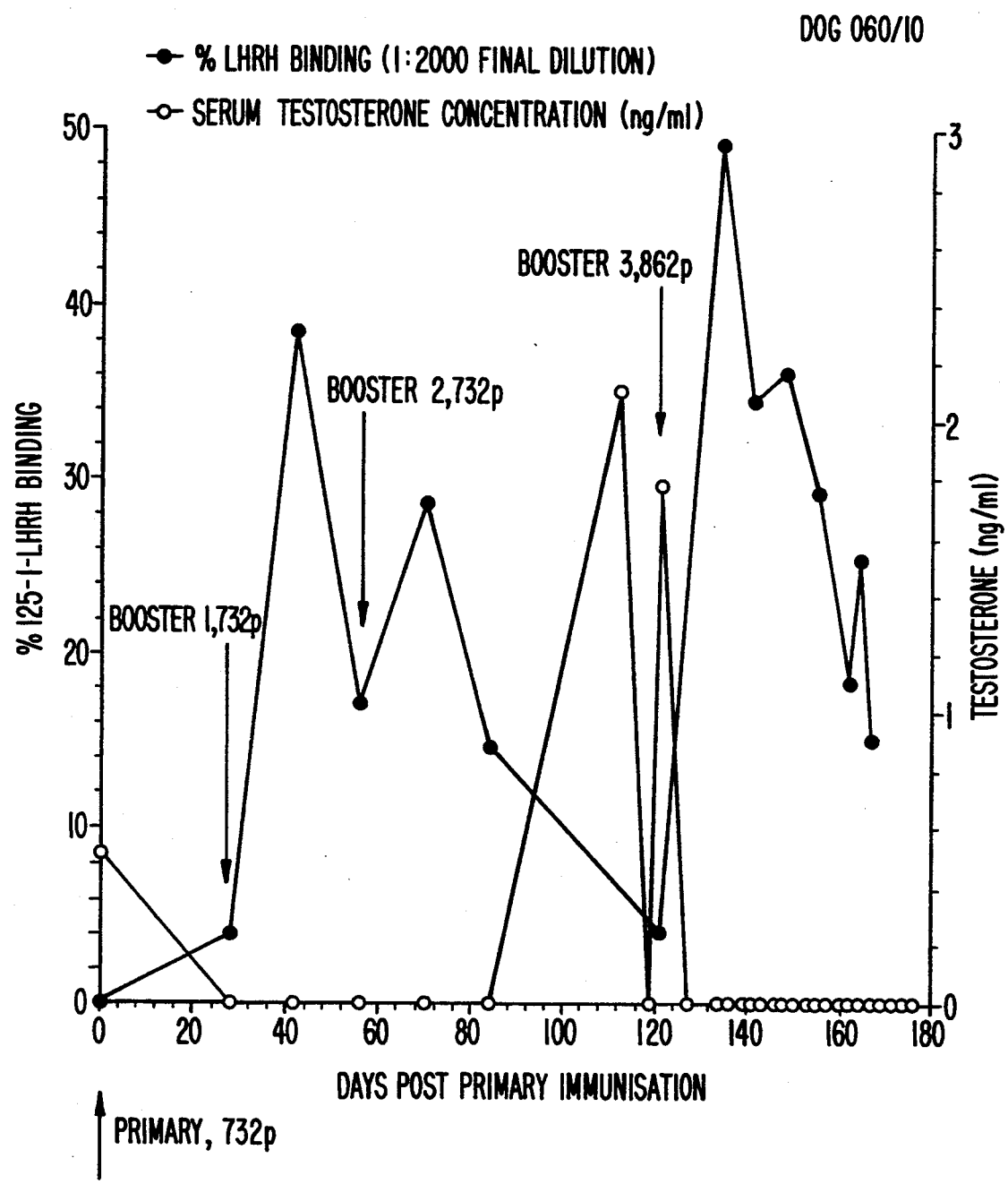

These results indicated that the immunisation of dogs with a fusion protein containing multiple copies of LHRH analogue, in saponin and SDS, was capable of evoking a strong LHRH antibody response. This response resulted in complete diminution of testosterone synthesis with concomitant castration effects indicated by the reduction in testis and prostate weights; testes; 3.2 vs 9.6 grams in control dogs; and prostate: 1.5 vs 9.2 grams in control dogs with comparable body weights ranging from 12.0 to 17.0 kilograms (FIG. 10). These data indicate that mixtures of fusion proteins for example 862p and 732p or derivatives of 732p may prove more efficacious than the administration of each alone.

Since the immunogenicity of the TraTp-LHRH analogue fusion proteins, formulated in saponin, was superior to that in alhydrogel or Montanide ISA-20, all subsequent work involving fusion protein constructs was performed using the saponin/SDS formulation.

EXAMPLE 6

T-CELL PROLIFERATIVE RESPONSES IN DOGS IMMUNIZED WITH TraTp-LHRH ANALOGUE FUSION PROTEINS WITH MULTIPLE LHRH ANALOGUE INSERTS.

In an attempt to enhance the immunogenicity of the LHRH analogue fusion proteins, we prepared constructs that would specify TraTp-LHRH analogue fusion proteins that contained one to eight LHRH analogue epitopes arranged in tandem. Following purification, the immunogenicity of the fusion proteins was tested in outbred mice and dogs.

Figure 9A:
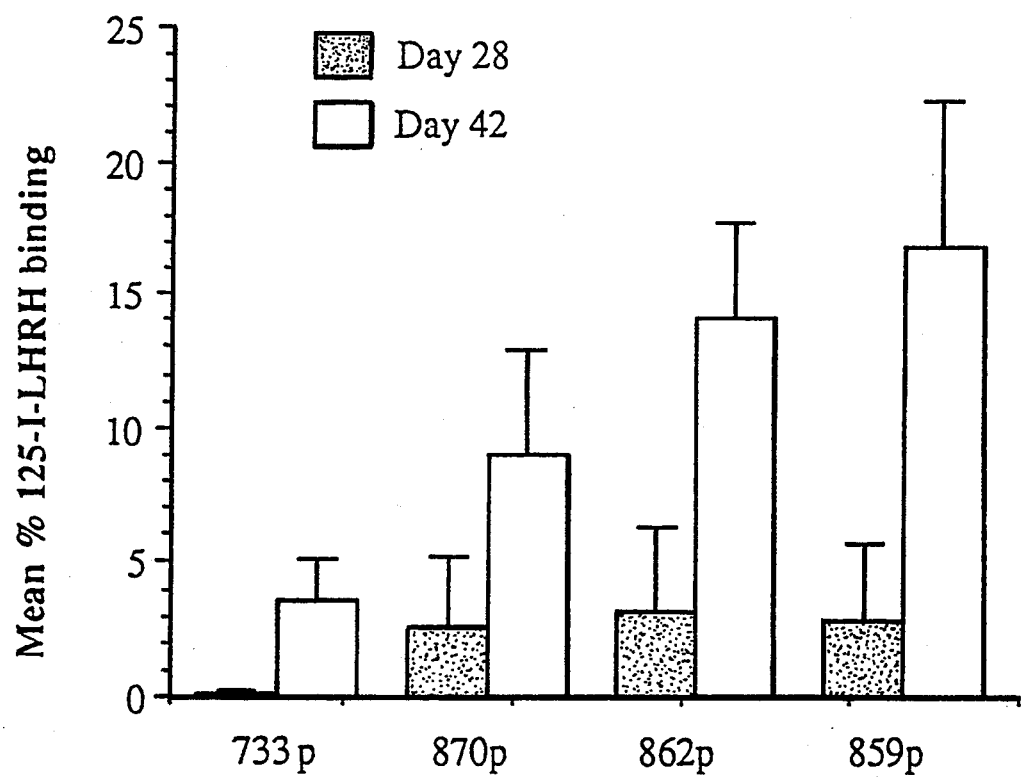

The results in FIG. 9A indicate that in the dog, fusion proteins with multiple inserts of LHRH analogue generated a higher anti-LHRH response (as measured by the binding of $^{125}$I-LHRH; at a serum dilution of 1:2000 final) than constructs with a single insert. Indeed, there was an increase in LHRH binding which corresponded to an increase in the number of LHRH analogue inserts per molecule of TraTp. With regard to T-cell proliferation, there was an increase (in terms of stimulation index) in the responses to LHRH, in vitro corresponding to the number of units of LHRH analogue in the carrier molecule (FIG. 11). The T-cell data therefore confirm the trend seen for the antibody response to LHRH (FIG. 11). TraTp-LHRH analogue fusions 733p (SEQ ID NO: 24), 870p (SEQ ID NO. 45), 862p (SEQ ID NO. 45) and 859p (SEQ ID NO: 47) refer to fusion proteins, containing one, two, four and eight LHRH analogue inserts respectively (as set forth in Sequence ID NO: 17, 29, 30 and 31 respectively), at the same site position in TraTp.

Outbred dogs (n=5 per group) were immunized intramuscularly on days 0 and 28 in two sites (0.5 ml per site); while outbred mice (ARC Swiss; n=10 per group) were immunized intramuscularly in two sites, but, giving 1/10th of the dose (0.05 ml per site) administered to the dogs, with the fusion proteins as follows:

Group 1: 733 (750 μg in 0.075% saponin and 0.1% SDS); Group 2: 870p (790 μg in 0.079% saponin and 0.1% SDS): Group 3: 862p (860 μg in 0.086% saponin and 0.1% SDS) and Group 4: 859p(1 mg in 0.1% saponin and 0.1% SDS). Mice received a tenth of this dose. In dogs heparinised and non-heparinised blood samples (5-10 ml) were collected from the jugular vein on Days 28 and 42 and T-cell proliferation, on Day 42, (was measured as described in a previous Section), and LHRH antibody response, on both Days 28 and 42; (as described in Example 4) were measured. In mice only the LHRH antibody response was measured in serum (0.4 ml of blood collected via the retro-orbital plexus route).

Figure 9B:
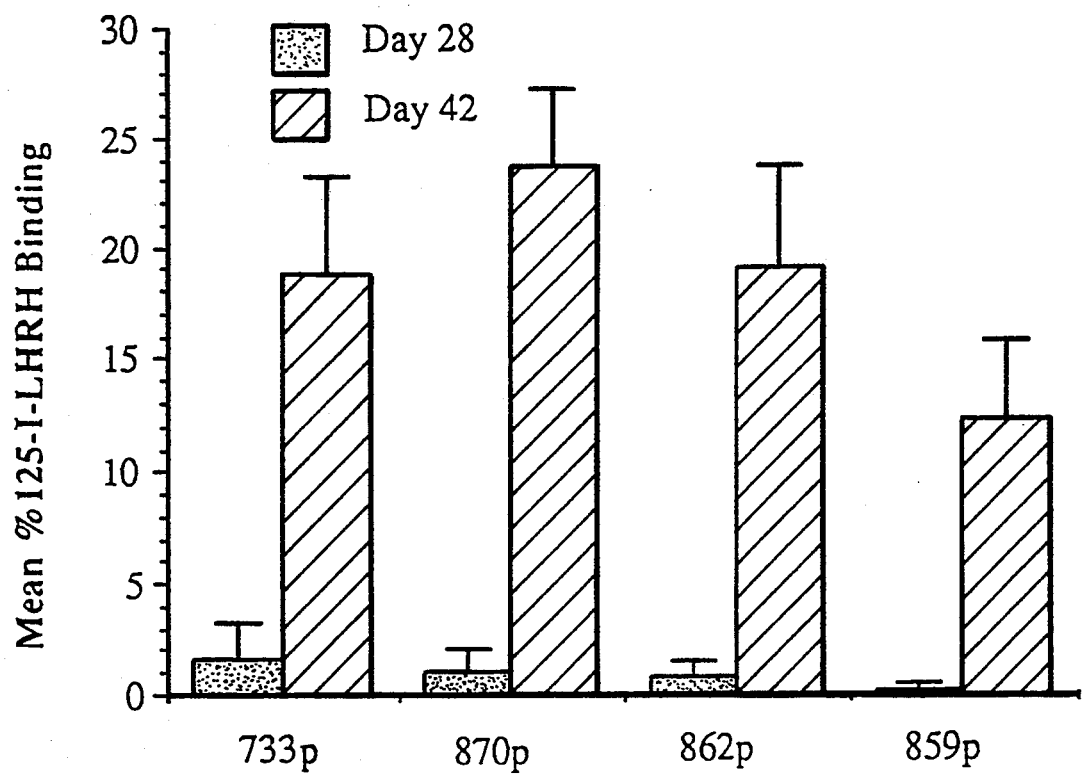

The results in FIG. 9A show that on Day 42 in the dog, fusion proteins with multiple inserts of LHRH analogue were considerably more immunogenic (evoking a higher anti-LHRH response) than constructs with a single insert. In fact, there was a progressive increase in LHRH binding corresponding to the number of LHRH analogue inserts per molecule of TraTp. In contrast, in the mouse, peak binding was seen in the sera of animals given the 870p TraTp-LHRH analogue fusion protein, while the 862p and 859p proteins elicited a somewhat lower level of LHRH binding response (FIG. 9B). On Day 28 (before the first booster) the levels of LHRH binding were low in both species although there was a suggestion that in the mouse, the binding response decreased with an increase in the number of LHRH analogue inserts in the TraTp molecule. In the dog, on the other hand, a slight increase in LHRH antibody levels corresponded to an increase in the LHRH analogue units in the fusion protein construct. These observations indicate that the introduction of multiple repeats of a peptide into the TraTp molecule considerably enhances the immunogenicity (ability to evoke a higher anti-peptide response) of the inserted peptide. Furthermore, the most effective immunogen for any particular species could not have been established a priori. Nevertheless, the principles and procedures now established by the present invention provide means to apply the technology to other species and fusion proteins of commercial interest.

Industrial Applicability

The fusion proteins of the invention are of use in providing self-adjuvanting immunogens which can be administered to a vertebrate host in a carrier such as a saline solution or saponin to immunise that host against endogenous LHRH so as to inhibit the reproductive function of the host.

Notwithstanding the specific uses exemplified in this specification, the approach used here with regard to LHRH analogue fusions suggests a means for providing fusion proteins comprising TraTp with other immunogenic epitopes, those epitopes including peptides of natural or synthetic origin, including fragments of proteins. The proteins may be hormones or growth factors such as LHRH, LH, FSH, chorionic gonadotrophin (CG), adrenocorticotrophic hormone (ACTH), somatotrophin, somatostatin, insulin-like growth factors, inhibin, activin, follistatin and variants thereof; they may be proteins of biological interest such as sperm antigens or ovum antigens such as zona pellucida antigens; alternatively, they may be antigens derived from parasite proteins, such parasites including protozoans, nematodes, cestodes, insects and ticks; they may also include antigens from bacteria or viruses, especially those protective against diseases in mammals, such diseases including cholera, AIDS, rabies, tetanus, smallpox, polio, diphtheria and others of commercial significance. It can be seen that in accordance with this invention fusion of TraTp and LHRH analogue sequences can be used to provide vaccines for immunising against LHRH and the present inventors believe that this approach could be extrapolated to the abovementioned further immunogenic epitopes on the basis of the teachings contained herein.

Deposition of Strains

E. coli strains have been deposited with the Australian Government Analytical Laboratories located at the Commonwealth Department of Administrative Services, New South Wales Regional Laboratory, 1 Suakin Street, Pymble, New South Wales 2073, Australia on 21 August 1990 in accordance with the Budapest Treaty under the following accession numbers:

| Strain No. | Accession No. |
|---|---|
| BTA 1665 | N90/031366 |
| BTA 1666 | N90/031367 |

| Strain No. | Accession No. |
|---|---|
| BTA 1907 | N90/031368 |

BTA 1349 carrying pBTA 439 was deposited with the American Type Culture Collection of 12301 Parklawn Drive, Rockville, Md. 20852, U.S.A. under accession number ATCC 67331 on 2 Mar. 1987, in accordance with the Budapest Treaty provisions.

TABLE 1

TraTp-LHRH Fusion proteins

| TraTp-LHRH Fusion | Plasmid pBTA # | E. Coli/ plasmid combination | Amino acid Insertion site in TraTp* | Number of LHRH Repeats |
|---|---|---|---|---|
| 609p | pBTA609 | BTA1905 | 30/31 | 1 |
| 730p | pBTA730 | BTA1663 | 241/242 | 1 |
| 731p | pBTA731 | BTA1664 | 220/221 | 1 |
| 732p | pBTA732 | BTA1665 | 80/81 | 1 |
| 733p | pBTA733 | BTA1666 | 200/201 | 1 |
| 734p | pBTA734 | BTA1667 | 175/176 | 1 |
| 735p | pBTA735 | BTA1668 | 101/102 | 1 |
| 736p | pBTA736 | BTA1669 | 80/81;220/221 | 1 at each site |
| 737p | pBTA737 | BTA1670 | 145/146 | 1 |
| 740p | pBTA740 | BTA1907 | 235/236 | 1 |
| 859p | pBTA859 | BTA2000 | 200/201 | 8 |
| 862p | pBTA862 | BTA2004 | 200/201 | 4 |
| 870p | pBTA870 | BTA2024 | 200/201 | 2 |

*Amino acid 1 is the Met 1 of the TraTp signal sequence shown in FIGS. 2A and 2B

TABLE 2

Antibodies raised in mice against TraTp-LHRH fusion proteins

| Protein | TraTp TITRES* | | LHRH TITRES* | | Mean $^{125}$I-LHRH binding (%) | | % Pregnant | |
|---|---|---|---|---|---|---|---|---|
|  | IF | SF | IF | SF | IF | SF | IF | SF |
| 730p | 2640 | 1520 | 100 | 100 | 7.4 | 0.0 | 83 | 100 |
| 731p | 9280 | 12800 | 100 | 100 | 0.1 | 1.56 | 80 | 60 |
| 732p | 1440 | 480 | 460 | 1920 | 0.0 | 64.3 | 40 | 0 |
| 733p | 12800 | 12800 | 360 | 1040 | 26.5 | 22.4 | 50 | 20 |
| 734p | 12800 | 12800 | 100 | 100 | 0.1 | 10.9 | 100 | 40 |
| 735p | 5120 | 7680 | 100 | 100 | 1.5 | 2.7 | 75 | 60 |
| 736p | 1920 | 500 | 100 | 720 | 0.4 | 17.4 | 50 | 25 |
| 737p | 12800 | 12800 | 100 | 100 | 0.0 | 0.0 | 100 | 60 |
| 740p | 2720 | 1360 | 360 | 380 | 52.9 | 65.4 | 50 | 0 |
| TraTp | 12800 | 12800 | 100 | 100 | 0.0 | 0.0 | 90 | 70 |

*ELISA titres are the reciprical of dilution to give O.D. = 0.5
Results are expressed as a percentage (%) of total radioactive counts added (minus the non-specific binding; NSB), to give a % of LHRH antibodies in the sera diluted 1: 2000 final.
IF = Insoluble Form (n = 5/group); SF = Soluble Form (n = 5/group).
Data are from sera taken at Day 42.
Males were introduced on Day 56 (after primary immunisation); mating was allowed over two cycles before withdrawing the males. Females were euthanased 10 days after this, and pregnancy status assessed.

We claim:

1. A fusion protein comprising TraTp (SEQ ID NO: 12) and at least one LHRH analogue, wherein at least one LHRH analogue is inserted into at least one of three sites in the sequence of TraTp (SEQ ID NO: 12), said sites being the sites located in the sequence of TraTp (SEQ ID NO: 12) between amino acid residues 80 and 81, residues 200 and 201, and residues 235 and 236, which fusion protein elicits the production of antibodies against LHRH when administered to a vertebrate host.

2. A fusion protein according to claim 1, wherein the LHRH analogue is as set forth in Sequence ID NO: 2.

3. A fusion protein according to claim 1, wherein the fusion protein is selected from 732p (SEQ ID NO: 16), 733p (SEQ ID NO: 24), 740p (SEQ ID NO: 28), 859p (SEQ. ID NO: 47), 862p (SEQ ID NO: 45), and 870p (SEQ ID NO: 43).

4. An isolated, purified polynucleotide comprising a region encoding a fusion protein according to claim 1.

5. A polynucleotide according to claim 4, wherein said polynucleotide is a plasmid.

6. A polynucleotide molecule according to claim 4, wherein said region encoding said fusion protein is operably linked to a $P_L$ promoter such that expression of said fusion protein is inducibly controlled by said promoter.

7. A polynucleotide molecule according to claim 5, wherein the plasmid vector is pBTA 812.

8. A polynucleotide molecule according to claim 4, wherein the polynucleotide molecule is a recombinant plasmid selected from the group consisting of: pBTA 732 (SEQ ID NOS. 15 and 16), pBTA 733 (SEQ ID NOS. 23 and 24), pBTA 740 (SEQ ID NOS. 27 and 28), pBTA 859 (SEQ ID NOS. 46 and 47), pBTA 862 (SEQ ID NOS. 44 and 45), and pBTA 870 (SEQ. ID NOS. 42 and 43).

9. A vaccine for contraceptive use comprising an effective dose of at least one fusion protein according to claim 1, together with a carrier, diluent, excipient and/or adjuvant suitable for human or veterinary use.

10. A vaccine according to claim 9 wherein the adjuvant is saponin.

11. A transformed cell comprising a polynucleotide molecule according to claim 4, wherein said polynucleotide molecule is self-replicating in said host cell and said fusion protein is inducibly expressed in said host cell.

12. A transformed cell according to claim 11, wherein the cell is an *E. coli* strain.

13. A transformed cell according to claim 11, wherein said transformed cell is selected from the group consisting of BTA 1665, BTA 1666, BTA 1907, BTA 2000, BTA 2004 and BTA 2024.

14. A method for inhibiting reproductive function in a vertebrate host comprising immunizing said host with a fusion protein according to claim 1.

15. A method according to claim 14, wherein said host is a domesticated mammal.

16. A method of inhibiting reproductive function in a vertibrate host comprising immunizing said host with a vaccine according to claim 9.

17. A method according to claim 16, wherein said host is a domesticated animal.

* * * * *

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( i x ) FEATURE:
( A ) NAME/KEY: Modified-site
( B ) LOCATION: 1
( D ) OTHER INFORMATION: /note="Represents pyroglutamic -continued acid"

( i x ) FEATURE:
    ( A ) NAME/KEY: Modified-site
    ( B ) LOCATION: 10
    ( D ) OTHER INFORMATION: /note="Represents glycinamide"

( x i ) SEQUENCE DESCRIPTION: SEQ ID NO:1:

```
Xaa His Trp Ser Tyr Gly Leu Arg Pro Xaa
1               5                   10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

```
Glu His Trp Ser Tyr Gly Leu Arg Pro Gly
1               5                   10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note="Represents pyroglutamic
            acid"

( i x ) FEATURE:
        ( A ) NAME/KEY: Modified-site
        ( B ) LOCATION: 10
        ( D ) OTHER INFORMATION: /note="Represents glycinamide"

( x i ) SEQUENCE DESCRIPTION: SEQ ID NO:3:

```
Xaa His Trp Ser Tyr Gly Leu Gln Pro Xaa
1               5                   10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 1
        ( D ) OTHER INFORMATION: /note="Represents pyroglutamic
            acid"

( i x ) FEATURE:
        ( A ) NAME/KEY: Modified-site
        ( B ) LOCATION: 10
        ( D ) OTHER INFORMATION: /note="Represents glycinamide"

( x i ) SEQUENCE DESCRIPTION: SEQ ID NO:4:

```
Xaa His Trp Ser His Gly Trp Tyr Pro Xaa
1               5                   10
```

( 2 ) INFORMATION FOR SEQ ID NO:5:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( i x ) FEATURE:
    ( A ) NAME/KEY: Modified-site
    ( B ) LOCATION: 1
    ( D ) OTHER INFORMATION: /note="Represents pyroglutamic acid"

( i x ) FEATURE:
    ( A ) NAME/KEY: Modified-site
    ( B ) LOCATION: 10
    ( D ) OTHER INFORMATION: /note="Represents glycinamide"

( x i ) SEQUENCE DESCRIPTION: SEQ ID NO:5:

```
Xaa His Trp Ser Tyr Gly Trp Leu Pro Xaa
1                 5                   10
```

( 2 ) INFORMATION FOR SEQ ID NO:6:

( i ) SEQUENCE CHARACTERISTICS:
    ( A ) LENGTH: 10 amino acids
    ( B ) TYPE: amino acid
    ( D ) TOPOLOGY: unknown ( i i ) MOLECULE TYPE: protein ( i x ) FEATURE:
    ( A ) NAME/KEY: Modified-site
    ( B ) LOCATION: 10
    ( D ) OTHER INFORMATION: /note="Represents glycinamide"

( x i ) SEQUENCE DESCRIPTION: SEQ ID NO:6:

```
Glu His Trp Ser Tyr Gly Leu Arg Pro Xaa
1                 5                   10
```

( 2 ) INFORMATION FOR SEQ ID NO:7:

( i ) SEQUENCE CHARACTERISTICS:
    ( A ) LENGTH: 10 amino acids
    ( B ) TYPE: amino acid
    ( D ) TOPOLOGY: unknown ( i i ) MOLECULE TYPE: protein ( i x ) FEATURE:
    ( A ) NAME/KEY: Modified-site
    ( B ) LOCATION: 10
    ( D ) OTHER INFORMATION: /note="Represents glycinamide"

( x i ) SEQUENCE DESCRIPTION: SEQ ID NO:7:

```
His His Trp Ser Tyr Gly Leu Arg Pro Xaa
1                 5                   10
```

( 2 ) INFORMATION FOR SEQ ID NO:8:

( i ) SEQUENCE CHARACTERISTICS:
    ( A ) LENGTH: 10 amino acids
    ( B ) TYPE: amino acid
    ( D ) TOPOLOGY: unknown ( i i ) MOLECULE TYPE: protein ( i x ) FEATURE:
    ( A ) NAME/KEY: Modified-site
    ( B ) LOCATION: 10
    ( D ) OTHER INFORMATION: /note="Represents glycinamide"

( x i ) SEQUENCE DESCRIPTION: SEQ ID NO:8:

```
Pro His Trp Ser Tyr Gly Leu Arg Pro Xaa
1                 5                   10
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: protein ( i x ) FEATURE:
        ( A ) NAME/KEY: Modified-site
        ( B ) LOCATION: 1
        ( D ) OTHER INFORMATION: /note="Represents pryoglutamic
            acid"

( i x ) FEATURE:
        ( A ) NAME/KEY: Modified-site
        ( B ) LOCATION: 10
        ( D ) OTHER INFORMATION: /note="Represents glycinamide"

( x i ) SEQUENCE DESCRIPTION: SEQ ID NO:9:

```
Xaa  His  Trp  Ser  Tyr  Lys  Leu  Arg  Pro  Xaa
 1              5                            10
```

( 2 ) INFORMATION FOR SEQ ID NO:10:

( i ) SEQUENCE CHARACTERISTICS:
        ( A ) LENGTH: 242 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: miscfeature
        ( B ) LOCATION: 143..148
        ( D ) OTHER INFORMATION: /note="Restriction site cleaved by
            Eco RI restriction endonuclease"

( x i ) SEQUENCE DESCRIPTION: SEQ ID NO:10:

```
AGATCTCTCA  CCTACCAAAC  AATGCCCCCC  TGCAAAAAAT  AAATTCATAT  AAAAAACATA      60
CAGATAACCA  TCTGCGGTGA  TAAATTATCT  CTGGCGGTGT  TGACATAAAT  ACCACTGGCG     120
GTGATACTGA  GCACATCAGC  AGGAATTCCC  AGCTCGATTA  TGGTTATAGT  TCAAAACGAT     180
ATGATGAGTG  AATCTTAATT  TGTATATTAT  GAGCTTTTAT  TCAATATGAA  GGAACATTGA     240
TG                                                                        242
```

( 2 ) INFORMATION FOR SEQ ID NO:11:

( i ) SEQUENCE CHARACTERISTICS:
        ( A ) LENGTH: 732 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: miscsignal
        ( B ) LOCATION: 1..60

( i x ) FEATURE:
        ( A ) NAME/KEY: miscfeature
        ( B ) LOCATION: 239..244
        ( D ) OTHER INFORMATION: /note="Restriction site cleaved by
            EcoR V restriction endonuclease"

( i x ) FEATURE:
        ( A ) NAME/KEY: miscfeature
        ( B ) LOCATION: 300..303
        ( D ) OTHER INFORMATION: /note="Restriction site cleaved by
            Hae III restriction endonuclease"

( i x ) FEATURE:
    ( A ) NAME/KEY: miscfeature
    ( B ) LOCATION: 432..437
    ( D ) OTHER INFORMATION: /note="Restriction site cleaved by
        Stu I restriction endonuclease"

( i x ) FEATURE:
    ( A ) NAME/KEY: miscfeature
    ( B ) LOCATION: 524..527
    ( D ) OTHER INFORMATION: /note="Restriction site cleaved by
        Rsa I restriction endonuclease"

( i x ) FEATURE:
    ( A ) NAME/KEY: miscfeature
    ( B ) LOCATION: 598..603
    ( D ) OTHER INFORMATION: /note="Restriction site cleaved by
        Sca I restriction endonuclease"

( i x ) FEATURE:
    ( A ) NAME/KEY: miscfeature
    ( B ) LOCATION: 658..663
    ( D ) OTHER INFORMATION: /note="Restriction site cleaved by
        Hpa I restriction endonuclease"

( i x ) FEATURE:
    ( A ) NAME/KEY: miscfeature
    ( B ) LOCATION: 704..709
    ( D ) OTHER INFORMATION: /note="Restriction site cleaved by
        Bal I restriction endonuclease"

( i x ) FEATURE:
    ( A ) NAME/KEY: miscfeature
    ( B ) LOCATION: 721..726
    ( D ) OTHER INFORMATION: /note="Restriction site cleaved by
        Ssp I restriction endonuclease"

( i x ) FEATURE:
    ( A ) NAME/KEY: CDS
    ( B ) LOCATION: 1..732

( x i ) SEQUENCE DESCRIPTION: SEQ ID NO:11:

```
ATG AAA ATG AAA AAA TTG ATG ATG GTT GCA CTG GTC AGT TCC ACT CTG      48
Met Lys Met Lys Lys Leu Met Met Val Ala Leu Val Ser Ser Thr Leu
 1               5                  10                  15

GCC CTT TCA GGG TGT GGT GCG ATG AGC ACA GCA ATC AAG AAG CGT AAC      96
Ala Leu Ser Gly Cys Gly Ala Met Ser Thr Ala Ile Lys Lys Arg Asn
             20                  25                  30

CTT GAG GTG AAG ACT CAG ATG AGT GAG ACC ATC TGG CTT GAA CCC GCC     144
Leu Glu Val Lys Thr Gln Met Ser Glu Thr Ile Trp Leu Glu Pro Ala
         35                  40                  45

AGC GAA CGC ACG GTA TTT CTG CAG ATC AAA AAC ACG TCT GAT AAA GAC     192
Ser Glu Arg Thr Val Phe Leu Gln Ile Lys Asn Thr Ser Asp Lys Asp
     50                  55                  60

ATG AGT GGG CTG CAG GGC AAA ATT GCT GAT GCT GTG AAA GCA AAA GGA     240
Met Ser Gly Leu Gln Gly Lys Ile Ala Asp Ala Val Lys Ala Lys Gly
 65                  70                  75                  80

TAT CAG GTG GTG ACT TCT CCG GAT AAA GCC TAC TAC TGG ATT CAG GCG     288
Tyr Gln Val Val Thr Ser Pro Asp Lys Ala Tyr Tyr Trp Ile Gln Ala
                 85                  90                  95

AAT GTG CTG AAG GCC GAT AAG ATG GAT CTG CGG GAG TCT CAG GGA TGG     336
Asn Val Leu Lys Ala Asp Lys Met Asp Leu Arg Glu Ser Gln Gly Trp
            100                 105                 110

CTG AAC CGT GGT TAT GAA GGC GCA GCA GTT GGT GCA GCG TTA GGT GCC     384
Leu Asn Arg Gly Tyr Glu Gly Ala Ala Val Gly Ala Ala Leu Gly Ala
        115                 120                 125

GGT ATT ACC GGT TAT AAC TCA AAT TCT GCC GGT GCC ACA CTC GGT GTA     432
Gly Ile Thr Gly Tyr Asn Ser Asn Ser Ala Gly Ala Thr Leu Gly Val
    130                 135                 140

GGC CTT GCT GCT GGT CTG GTG GGT ATG GCT GCA GAT GCG ATG GTG GAA     480
Gly Leu Ala Ala Gly Leu Val Gly Met Ala Ala Asp Ala Met Val Glu
145                 150                 155                 160
```

```
GAT GTG AAC TAT ACC ATG ATC ACG GAT GTA CAG ATT GCA GAG CGT ACT            528
Asp Val Asn Tyr Thr Met Ile Thr Asp Val Gln Ile Ala Glu Arg Thr
            165             170             175

AAG GCA ACG GTG ACA ACG GAT AAT GTT GCC GCC CTG CGT CAG GGC ACA            576
Lys Ala Thr Val Thr Thr Asp Asn Val Ala Ala Leu Arg Gln Gly Thr
            180             185             190

TCA GGT GCG AAA ATT CAG ACC AGT ACT GAA ACA GGT AAC CAG CAT AAA            624
Ser Gly Ala Lys Ile Gln Thr Ser Thr Glu Thr Gly Asn Gln His Lys
            195             200             205

TAC CAG ACC CGT GTG GTT TCA AAT GCG AAC AAG GTT AAC CTG AAA TTT            672
Tyr Gln Thr Arg Val Val Ser Asn Ala Asn Lys Val Asn Leu Lys Phe
            210             215             220

GAA GAG GCG AAG CCT GTT CTC GAA GAC CAA CTG GCC AAA TCA ATC GCA            720
Glu Glu Ala Lys Pro Val Leu Glu Asp Gln Leu Ala Lys Ser Ile Ala
225             230             235             240

AAT ATT CTC TGA                                                            732
Asn Ile Leu
```

( 2 ) INFORMATION FOR SEQ ID NO:12:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Lys Met Lys Lys Leu Met Met Val Ala Leu Val Ser Ser Thr Leu
1               5                   10                  15

Ala Leu Ser Gly Cys Gly Ala Met Ser Thr Ala Ile Lys Lys Arg Asn
                20                  25                  30

Leu Glu Val Lys Thr Gln Met Ser Glu Thr Ile Trp Leu Glu Pro Ala
            35                  40                  45

Ser Glu Arg Thr Val Phe Leu Gln Ile Lys Asn Thr Ser Asp Lys Asp
        50                  55                  60

Met Ser Gly Leu Gln Gly Lys Ile Ala Asp Ala Val Lys Ala Lys Gly
65                  70                  75                  80

Tyr Gln Val Val Thr Ser Pro Asp Lys Ala Tyr Tyr Trp Ile Gln Ala
                85                  90                  95

Asn Val Leu Lys Ala Asp Lys Met Asp Leu Arg Glu Ser Gln Gly Trp
                100                 105                 110

Leu Asn Arg Gly Tyr Glu Gly Ala Ala Val Gly Ala Ala Leu Gly Ala
            115                 120                 125

Gly Ile Thr Gly Tyr Asn Ser Asn Ser Ala Gly Ala Thr Leu Gly Val
    130                 135                 140

Gly Leu Ala Ala Gly Leu Val Gly Met Ala Ala Asp Ala Met Val Glu
145                 150                 155                 160

Asp Val Asn Tyr Thr Met Ile Thr Asp Val Gln Ile Ala Glu Arg Thr
                165                 170                 175

Lys Ala Thr Val Thr Thr Asp Asn Val Ala Ala Leu Arg Gln Gly Thr
            180                 185                 190

Ser Gly Ala Lys Ile Gln Thr Ser Thr Glu Thr Gly Asn Gln His Lys
        195                 200                 205

Tyr Gln Thr Arg Val Val Ser Asn Ala Asn Lys Val Asn Leu Lys Phe
    210                 215                 220

Glu Glu Ala Lys Pro Val Leu Glu Asp Gln Leu Ala Lys Ser Ile Ala
225                 230                 235                 240

Asn Ile Leu
```

( 2 ) INFORMATION FOR SEQ ID NO:13:

( i ) SEQUENCE CHARACTERISTICS:
      ( A ) LENGTH: 48 base pairs
      ( B ) TYPE: nucleic acid
      ( C ) STRANDEDNESS: double
      ( D ) TOPOLOGY: linear ( i i ) MOLECULE TYPE: Other nucleic acid;
      ( A ) DESCRIPTION: Synthetic DNA ( v i i ) IMMEDIATE SOURCE:
      ( B ) CLONE: pBTA 609

( i x ) FEATURE:
      ( A ) NAME/KEY: CDS
      ( B ) LOCATION: 1..48

( i x ) FEATURE:
      ( A ) NAME/KEY: miscfeature
      ( B ) LOCATION: 10..39
      ( D ) OTHER INFORMATION: /note="Coding sequence for LHRH
            analogue"

( x i ) SEQUENCE DESCRIPTION: SEQ ID NO:13:

```
AAG  AAG  CAG  GAG  CAC  TGG  TCA  TAT  GGT  CTG  CGT  CCC  GGG  CTG  CTT  GAG      48
Lys  Lys  Gln  Glu  His  Trp  Ser  Tyr  Gly  Leu  Arg  Pro  Gly  Leu  Leu  Glu
 1                    5                        10                       15
```

( 2 ) INFORMATION FOR SEQ ID NO:14:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: protein ( x i ) SEQUENCE DESCRIPTION: SEQ ID NO:14:

```
Lys  Lys  Gln  Glu  His  Trp  Ser  Tyr  Gly  Leu  Arg  Pro  Gly  Leu  Leu  Glu
 1                    5                        10                       15
```

( 2 ) INFORMATION FOR SEQ ID NO:15:

( i ) SEQUENCE CHARACTERISTICS:
      ( A ) LENGTH: 51 base pairs
      ( B ) TYPE: nucleic acid
      ( C ) STRANDEDNESS: double
      ( D ) TOPOLOGY: linear ( i i ) MOLECULE TYPE: Other nucleic acid;
      ( A ) DESCRIPTION: Synthetic DNA ( v i i ) IMMEDIATE SOURCE:
      ( B ) CLONE: pBTA 732

( i x ) FEATURE:
      ( A ) NAME/KEY: miscfeature
      ( B ) LOCATION: 13..42
      ( D ) OTHER INFORMATION: /note="Coding sequence for LHRH
            analogue"

( i x ) FEATURE:
      ( A ) NAME/KEY: CDS
      ( B ) LOCATION: 1..51

( x i ) SEQUENCE DESCRIPTION: SEQ ID NO:15:

```
AAA  GGA  TCC  CCC  GAG  CAC  TGG  TCA  TAT  GGT  CTG  CGT  CCC  GGG  GAG  CAT      48
Lys  Gly  Ser  Pro  Glu  His  Trp  Ser  Tyr  Gly  Leu  Arg  Pro  Gly  Glu  His
 1                    5                        10                       15

CAG                                                                                  51
Gln
```

( 2 ) INFORMATION FOR SEQ ID NO:16:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Lys Gly Ser Pro Glu His Trp Ser Tyr Gly Leu Arg Pro Gly Glu His
 1               5                   10                  15
Gln
```

( 2 ) INFORMATION FOR SEQ ID NO:17:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( v i i ) IMMEDIATE SOURCE:
        ( B ) CLONE: pBTA 735

( i x ) FEATURE:
        ( A ) NAME/KEY: miscfeature
        ( B ) LOCATION: 13..42
        ( D ) OTHER INFORMATION: /note="Coding sequence for LHRH
            analogue"

( i x ) FEATURE:
        ( A ) NAME/KEY: CDS
        ( B ) LOCATION: 1..51

( x i ) SEQUENCE DESCRIPTION: SEQ ID NO:17:

```
AAG GCC CCC GAG CAC TGG TCA TAT GGT CTG CGT CCC GGG GGG AGC TCC    48
Lys Ala Pro Glu His Trp Ser Tyr Gly Leu Arg Pro Gly Gly Ser Ser
 1               5                   10                  15

GAT                                                                51
Asp
```

( 2 ) INFORMATION FOR SEQ ID NO:18:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Lys Ala Pro Glu His Trp Ser Tyr Gly Leu Arg Pro Gly Gly Ser Ser
 1               5                   10                  15
Asp
```

( 2 ) INFORMATION FOR SEQ ID NO:19:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( v i i ) IMMEDIATE SOURCE:
        ( B ) CLONE: pBTA 737

(i x) FEATURE:
    (A) NAME/KEY: miscfeature
    (B) LOCATION: 13..42
    (D) OTHER INFORMATION: /note="Coding sequence for LHRH
        analogue"

(i x) FEATURE:
    (A) NAME/KEY: CDS
    (B) LOCATION: 1..54

(x i) SEQUENCE DESCRIPTION: SEQ ID NO:19:

| GTA | GGA | GCT | CCC | GAG | CAC | TGG | TCA | TAT | GGT | CTG | CGT | CCC | GGG | GGG | GGC | 48 |
|---|---|---|---|---|---|---|---|---|---|---|---|---|---|---|---|---|
| Val | Gly | Ala | Pro | Glu | His | Trp | Ser | Tyr | Gly | Leu | Arg | Pro | Gly | Gly | Gly | |
| 1 | | | | 5 | | | | | 10 | | | | | 15 | | |

| CTT | GCT | 54 |
|---|---|---|
| Leu | Ala | |

(2) INFORMATION FOR SEQ ID NO:20:

(i) SEQUENCE CHARACTERISTICS:
        (A) LENGTH: 18 amino acids
        (B) TYPE: amino acid
        (D) TOPOLOGY: linear (ii) MOLECULE TYPE: protein (x i) SEQUENCE DESCRIPTION: SEQ ID NO:20:

| Val | Gly | Ala | Pro | Glu | His | Trp | Ser | Tyr | Gly | Leu | Arg | Pro | Gly | Gly | Gly |
|---|---|---|---|---|---|---|---|---|---|---|---|---|---|---|---|
| 1 | | | | 5 | | | | | 10 | | | | | 15 | |

Leu Ala (2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: Other nucleic acid;
        (A) DESCRIPTION: Synthetic DNA (vii) IMMEDIATE SOURCE:
        (B) CLONE: pBTA 734

(ix) FEATURE:
        (A) NAME/KEY: CDS
        (B) LOCATION: 1..42

(ix) FEATURE:
        (A) NAME/KEY: miscfeature
        (B) LOCATION: 7..36
        (D) OTHER INFORMATION: /note="Coding sequence for LHRH
            analogue"

(x i) SEQUENCE DESCRIPTION: SEQ ID NO:21:

| GAG | CGT | GAG | CAC | TGG | TCA | TAT | GGT | CTG | CGT | CCC | GGG | ACT | AAG | 42 |
|---|---|---|---|---|---|---|---|---|---|---|---|---|---|---|
| Glu | Arg | Glu | His | Trp | Ser | Tyr | Gly | Leu | Arg | Pro | Gly | Thr | Lys | |
| 1 | | | | 5 | | | | | 10 | | | | | |

(2) INFORMATION FOR SEQ ID NO:22:

(i) SEQUENCE CHARACTERISTICS:
        (A) LENGTH: 14 amino acids
        (B) TYPE: amino acid
        (D) TOPOLOGY: linear (ii) MOLECULE TYPE: protein (x i) SEQUENCE DESCRIPTION: SEQ ID NO:22:

| Glu | Arg | Glu | His | Trp | Ser | Tyr | Gly | Leu | Arg | Pro | Gly | Thr | Lys |
|---|---|---|---|---|---|---|---|---|---|---|---|---|---|
| 1 | | | | 5 | | | | | 10 | | | | |

( 2 ) INFORMATION FOR SEQ ID NO:23:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( v i i ) IMMEDIATE SOURCE:
        ( B ) CLONE: pBTA 733

( i x ) FEATURE:
        ( A ) NAME/KEY: CDS
        ( B ) LOCATION: 1..42

( i x ) FEATURE:
        ( A ) NAME/KEY: miscfeature
        ( B ) LOCATION: 7..36
        ( D ) OTHER INFORMATION: /note="Coding sequence for LHRH
            analogue"

( x i ) SEQUENCE DESCRIPTION: SEQ ID NO:23:

```
ACC AGT GAG CAC TGG TCA TAT GGT CTG CGT CCC GGG ACT GAA        42
Thr Ser Glu His Trp Ser Tyr Gly Leu Arg Pro Gly Thr Glu
 1           5                       10
```

( 2 ) INFORMATION FOR SEQ ID NO:24:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Thr Ser Glu His Trp Ser Tyr Gly Leu Arg Pro Gly Thr Glu
 1           5                       10
```

( 2 ) INFORMATION FOR SEQ ID NO:25:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( v i i ) IMMEDIATE SOURCE:
        ( B ) CLONE: pBTA 731

( i x ) FEATURE:
        ( A ) NAME/KEY: CDS
        ( B ) LOCATION: 1..42

( i x ) FEATURE:
        ( A ) NAME/KEY: miscfeature
        ( B ) LOCATION: 7..36
        ( D ) OTHER INFORMATION: /note="Coding sequence for LHRH
            analogue"

( x i ) SEQUENCE DESCRIPTION: SEQ ID NO:25:

```
AAG GTT GAG CAC TGG TCA TAT GGT CTG CGT CCC GGG AAC CTG        42
Lys Val Glu His Trp Ser Tyr Gly Leu Arg Pro Gly Asn Leu
 1           5                       10
```

( 2 ) INFORMATION FOR SEQ ID NO:26:

( i ) SEQUENCE CHARACTERISTICS:
        ( A ) LENGTH: 14 amino acids (B) TYPE: amino acid
(D) TOPOLOGY: linear (ii) MOLECULE TYPE: protein (xi) SEQUENCE DESCRIPTION: SEQ ID NO:26:

```
Lys Val Glu His Trp Ser Tyr Gly Leu Arg Pro Gly Asn Leu
 1               5                   10
```

(2) INFORMATION FOR SEQ ID NO:27:

(i) SEQUENCE CHARACTERISTICS:
(A) LENGTH: 54 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA (vii) IMMEDIATE SOURCE:
(B) CLONE: pBTA 740

(ix) FEATURE:
(A) NAME/KEY: CDS
(B) LOCATION: 1..54

(ix) FEATURE:
(A) NAME/KEY: miscfeature
(B) LOCATION: 13..42
(D) OTHER INFORMATION: /note="Coding sequence for LHRH analogue"

(xi) SEQUENCE DESCRIPTION: SEQ ID NO:27:

```
CAA CTG GCC CCC GAG CAC TGG TCA TAT GGT CTG CGT CCC GGG GGG AGC    48
Gln Leu Ala Pro Glu His Trp Ser Tyr Gly Leu Arg Pro Gly Gly Ser
 1               5                   10                  15

TCC AAA                                                             54
Ser Lys
```

(2) INFORMATION FOR SEQ ID NO:28:

(i) SEQUENCE CHARACTERISTICS:
(A) LENGTH: 18 amino acids
(B) TYPE: amino acid
(D) TOPOLOGY: linear (ii) MOLECULE TYPE: protein (xi) SEQUENCE DESCRIPTION: SEQ ID NO:28:

```
Gln Leu Ala Pro Glu His Trp Ser Tyr Gly Leu Arg Pro Gly Gly Ser
 1               5                   10                  15
Ser Lys
```

(2) INFORMATION FOR SEQ ID NO:29:

(i) SEQUENCE CHARACTERISTICS:
(A) LENGTH: 45 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA (vii) IMMEDIATE SOURCE:
(B) CLONE: pBTA 730

(ix) FEATURE:
(A) NAME/KEY: CDS
(B) LOCATION: 1..45

(ix) FEATURE:
(A) NAME/KEY: miscfeature ( B ) LOCATION: 7..36
( D ) OTHER INFORMATION: /note="Coding sequence for LHRH analogue"

( x i ) SEQUENCE DESCRIPTION: SEQ ID NO:29:

| GCA | AAT | GAG | CAC | TGG | TCA | TAT | GGT | CTG | CGT | CCC | GGG | ATT | CTC | TGA | 45 |
| Ala | Asn | Glu | His | Trp | Ser | Tyr | Gly | Leu | Arg | Pro | Gly | Ile | Leu | | |
| 1 | | | | 5 | | | | | 10 | | | | | 15 | |

( 2 ) INFORMATION FOR SEQ ID NO:30:

( i ) SEQUENCE CHARACTERISTICS:
( A ) LENGTH: 14 amino acids
( B ) TYPE: amino acid
( D ) TOPOLOGY: linear ( i i ) MOLECULE TYPE: protein ( x i ) SEQUENCE DESCRIPTION: SEQ ID NO:30:

Ala Asn Glu His Trp Ser Tyr Gly Leu Arg Pro Gly Ile Leu
1               5                   10

( 2 ) INFORMATION FOR SEQ ID NO:31:

( i ) SEQUENCE CHARACTERISTICS:
( A ) LENGTH: 30 base pairs
( B ) TYPE: nucleic acid
( C ) STRANDEDNESS: double
( D ) TOPOLOGY: linear ( i i ) MOLECULE TYPE: Other nucleic acid;
( A ) DESCRIPTION: Synthetic DNA ( i x ) FEATURE:
( A ) NAME/KEY: CDS
( B ) LOCATION: 1..30

( i x ) FEATURE:
( A ) NAME/KEY: miscfeature
( B ) LOCATION: 25..30
( D ) OTHER INFORMATION: /note="Restriction site cleaved by Sma I restriction endonuclease"

( x i ) SEQUENCE DESCRIPTION: SEQ ID NO:31:

| GAG | CAC | TGG | TCA | TAT | GGT | CTG | CGT | CCC | GGG | 30 |
| Glu | His | Trp | Ser | Tyr | Gly | Leu | Arg | Pro | Gly | |
| 1 | | | | 5 | | | | | 10 | |

( 2 ) INFORMATION FOR SEQ ID NO:32:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( x i ) SEQUENCE DESCRIPTION: SEQ ID NO:32:

Glu His Trp Ser Tyr Gly Leu Arg Pro Gly
1               5                   10

( 2 ) INFORMATION FOR SEQ ID NO:33:

( i ) SEQUENCE CHARACTERISTICS:
( A ) LENGTH: 30 base pairs
( B ) TYPE: nucleic acid
( C ) STRANDEDNESS: double
( D ) TOPOLOGY: linear ( i i ) MOLECULE TYPE: Other nucleic acid;
( A ) DESCRIPTION: Synthetic DNA ( i v ) ANTI-SENSE: YES ( x i ) SEQUENCE DESCRIPTION: SEQ ID NO:33:

CCCGGGACGC AGACCATATG ACCAGTGCTG 30

( 2 ) INFORMATION FOR SEQ ID NO:34:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Linker DNA sequence ( i x ) FEATURE:
        ( A ) NAME/KEY: miscfeature
        ( B ) LOCATION: 3..8
        ( D ) OTHER INFORMATION: /note="Restriction site cleaved by
        Sma I restriction endonuclease"

( x i ) SEQUENCE DESCRIPTION: SEQ ID NO:34:

CCCCCGGGAG CT 12

( 2 ) INFORMATION FOR SEQ ID NO:35:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Linker DNA sequence ( i v ) ANTI-SENSE: YES ( x i ) SEQUENCE DESCRIPTION: SEQ ID NO:35:

AGCTCCCGGG GG 12

( 2 ) INFORMATION FOR SEQ ID NO:36:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( i x ) FEATURE:
        ( A ) NAME/KEY: CDS
        ( B ) LOCATION: 1..30
        ( D ) OTHER INFORMATION: /note="Encodes LHRH analogue used
        in the construction of pBTA 870"

( x i ) SEQUENCE DESCRIPTION: SEQ ID NO:36:

```
GGT GAA CAT TGG AGC TAC GGT CTA CGC CCC          30
Gly Glu His Trp Ser Tyr Gly Leu Arg Pro
 1               5                   10
```

( 2 ) INFORMATION FOR SEQ ID NO:37:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

```
Gly Glu His Trp Ser Tyr Gly Leu Arg Pro
 1               5                   10
```

( 2 ) INFORMATION FOR SEQ ID NO:38:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( i v ) ANTI-SENSE: YES ( x i ) SEQUENCE DESCRIPTION: SEQ ID NO:38:

GGGGCGTAGA CCGTAGCTCC AATGTTCACC                                    30

( 2 ) INFORMATION FOR SEQ ID NO:39:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( i x ) FEATURE:
        ( A ) NAME/KEY: CDS
        ( B ) LOCATION: 1..60
        ( D ) OTHER INFORMATION: /note="Encodes LHRH dimer analogue
            used in the construction of pBTA 862"

( x i ) SEQUENCE DESCRIPTION: SEQ ID NO:39:

```
GGT GAA CAC TGG TCT TAT GGC TTA CGG CCG GGA GAG CAT TGG AGT TAC      48
Gly Glu His Trp Ser Tyr Gly Leu Arg Pro Gly Glu His Trp Ser Tyr
 1               5                  10                  15

GGC CTC CGT CCC                                                      60
Gly Leu Arg Pro
            20
```

( 2 ) INFORMATION FOR SEQ ID NO:40:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Gly Glu His Trp Ser Tyr Gly Leu Arg Pro Gly Glu His Trp Ser Tyr
 1               5                  10                  15

Gly Leu Arg Pro
            20
```

( 2 ) INFORMATION FOR SEQ ID NO:41:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( i v ) ANTI-SENSE: YES ( x i ) SEQUENCE DESCRIPTION: SEQ ID NO:41:

GGGACGGAGG CCGTAACTCC AATGCTCTCC CGGCCGTAAG CCATAAGACC AGTGTTCACC    60

( 2 ) INFORMATION FOR SEQ ID NO:42:

( i ) SEQUENCE CHARACTERISTICS:
        ( A ) LENGTH: 72 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( v i i ) IMMEDIATE SOURCE:
        ( B ) CLONE: pBTA 870

( i x ) FEATURE:
        ( A ) NAME/KEY: CDS
        ( B ) LOCATION: 1..72

( i x ) FEATURE:
        ( A ) NAME/KEY: miscfeature
        ( B ) LOCATION: 7..66
        ( D ) OTHER INFORMATION: /note="Encodes LHRH analogue dimer"

( x i ) SEQUENCE DESCRIPTION: SEQ ID NO:42:

```
ACC AGT GAG CAC TGG TCA TAT GGT CTG CGT CCC GGT GAA CAT TGG AGC        48
Thr Ser Glu His Trp Ser Tyr Gly Leu Arg Pro Gly Glu His Trp Ser
  1               5                  10                  15

TAC GGT CTA CGC CCC GGG ACT GAA                                        72
Tyr Gly Leu Arg Pro Gly Thr Glu
             20
```

( 2 ) INFORMATION FOR SEQ ID NO:43:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

```
Thr Ser Glu His Trp Ser Tyr Gly Leu Arg Pro Gly Glu His Trp Ser
  1               5                  10                  15

Tyr Gly Leu Arg Pro Gly Thr Glu
             20
```

( 2 ) INFORMATION FOR SEQ ID NO:44:

( i ) SEQUENCE CHARACTERISTICS:
        ( A ) LENGTH: 132 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( v i i ) IMMEDIATE SOURCE:
        ( A ) LIBRARY: pBTA 862

( i x ) FEATURE:
        ( A ) NAME/KEY: CDS
        ( B ) LOCATION: 1..132

( i x ) FEATURE:
        ( A ) NAME/KEY: miscfeature
        ( B ) LOCATION: 7..126
        ( D ) OTHER INFORMATION: /note="Encodes LHRH analogue tetramer"

( x i ) SEQUENCE DESCRIPTION: SEQ ID NO:44:

```
ACC AGT GAG CAC TGG TCA TAT GGT CTG CGT CCC GGT GAA CAT TGG AGC        48
```

```
Thr Ser Glu His Trp Ser Tyr Gly Leu Arg Pro Gly Glu His Trp Ser
 1               5                  10                  15

TAC GGT CTA CGC CCC GGT GAA CAC TGG TCT TAT GGC TTA CGG CCG GGA        96
Tyr Gly Leu Arg Pro Gly Glu His Trp Ser Tyr Gly Leu Arg Pro Gly
                20                  25                  30

GAG CAT TGG AGT TAC GGC CTC CGT CCC GGG ACT GAA                       132
Glu His Trp Ser Tyr Gly Leu Arg Pro Gly Thr Glu
        35                  40
```

( 2 ) INFORMATION FOR SEQ ID NO:45:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Thr Ser Glu His Trp Ser Tyr Gly Leu Arg Pro Gly Glu His Trp Ser
 1               5                  10                  15

Tyr Gly Leu Arg Pro Gly Glu His Trp Ser Tyr Gly Leu Arg Pro Gly
                20                  25                  30

Glu His Trp Ser Tyr Gly Leu Arg Pro Gly Thr Glu
        35                  40
```

( 2 ) INFORMATION FOR SEQ ID NO:46:

( i ) SEQUENCE CHARACTERISTICS:
        ( A ) LENGTH: 252 base pairs
        ( B ) TYPE: nucleic acid
        ( C ) STRANDEDNESS: double
        ( D ) TOPOLOGY: linear ( i i ) MOLECULE TYPE: Other nucleic acid;
        ( A ) DESCRIPTION: Synthetic DNA ( v i i ) IMMEDIATE SOURCE:
        ( B ) CLONE: pBTA 859

( i x ) FEATURE:
        ( A ) NAME/KEY: CDS
        ( B ) LOCATION: 1..252

( i x ) FEATURE:
        ( A ) NAME/KEY: miscfeature
        ( B ) LOCATION: 7..246
        ( D ) OTHER INFORMATION: /note="Encodes LHRH analogue octamer"

( x i ) SEQUENCE DESCRIPTION: SEQ ID NO:46:

```
ACC AGT GAG CAC TGG TCA TAT GGT CTG CGT CCC GGT GAA CAT TGG AGC        48
Thr Ser Glu His Trp Ser Tyr Gly Leu Arg Pro Gly Glu His Trp Ser
 1               5                  10                  15

TAC GGT CTA CGC CCC GGT GAA CAC TGG TCT TAT GGC TTA CGG CCG GGA        96
Tyr Gly Leu Arg Pro Gly Glu His Trp Ser Tyr Gly Leu Arg Pro Gly
                20                  25                  30

GAG CAT TGG AGT TAC GGC CTC CGT CCC GGT GAA CAC TGG TCT TAT GGC       144
Glu His Trp Ser Tyr Gly Leu Arg Pro Gly Glu His Trp Ser Tyr Gly
        35                  40                  45

TTA CGG CCG GGA GAG CAT TGG AGT TAC GGC CTC CGT CCC GGT GAA CAC       192
Leu Arg Pro Gly Glu His Trp Ser Tyr Gly Leu Arg Pro Gly Glu His
        50                  55                  60

TGG TCT TAT GGC TTA CGG CCG GGA GAG CAT TGG AGT TAC GGC CTC CGT       240
Trp Ser Tyr Gly Leu Arg Pro Gly Glu His Trp Ser Tyr Gly Leu Arg
 65              70                  75                  80

CCC GGG ACT GAA                                                       252
Pro Gly Thr Glu
```

( 2 ) INFORMATION FOR SEQ ID NO:47:

( i ) SEQUENCE CHARACTERISTICS:
       ( A ) LENGTH: 84 amino acids
       ( B ) TYPE: amino acid
       ( D ) TOPOLOGY: linear ( i i ) MOLECULE TYPE: protein ( x i ) SEQUENCE DESCRIPTION: SEQ ID NO:47:

```
Thr Ser Glu His Trp Ser Tyr Gly Leu Arg Pro Gly Glu His Trp Ser
 1               5                  10                  15
Tyr Gly Leu Arg Pro Gly Glu His Trp Ser Tyr Gly Leu Arg Pro Gly
             20                  25                  30
Glu His Trp Ser Tyr Gly Leu Arg Pro Gly Glu His Trp Ser Tyr Gly
         35                  40                  45
Leu Arg Pro Gly Glu His Trp Ser Tyr Gly Leu Arg Pro Gly Glu His
     50                  55                  60
Trp Ser Tyr Gly Leu Arg Pro Gly Glu His Trp Ser Tyr Gly Leu Arg
 65                  70                  75                  80
Pro Gly Thr Glu
```